(12) United States Patent
Chen et al.

(10) Patent No.: US 12,430,567 B2
(45) Date of Patent: Sep. 30, 2025

(54) MULTIPLEX SIMILARITY SEARCH IN DNA DATA STORAGE

(71) Applicant: Microsoft Technology Licensing, LLC, Redmond, WA (US)

(72) Inventors: Yuan-Jyue Chen, Taipei (TW); Karin Strauss, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1215 days.

(21) Appl. No.: 16/540,812

(22) Filed: Aug. 14, 2019

(65) Prior Publication Data

US 2021/0050073 A1 Feb. 18, 2021

(51) Int. Cl.
*G06N 3/123* (2023.01)
*C40B 40/06* (2006.01)
*G06F 16/245* (2019.01)
*G16B 25/00* (2019.01)
*G16B 30/10* (2019.01)
(Continued)

(52) U.S. Cl.
CPC ............. *G06N 3/123* (2013.01); *C40B 40/06* (2013.01); *G06F 16/245* (2019.01); *G16B 25/00* (2019.02); *G16B 30/10* (2019.02); *G16B 45/00* (2019.02); *G16B 50/30* (2019.02)

(58) Field of Classification Search
None
See application file for complete search history.

(56) References Cited

U.S. PATENT DOCUMENTS 9,898,579 B2 2/2018 Strauss et al.
2016/0362726 A1* 12/2016 Makarov et al. ........ C12Q 1/68
(Continued)

FOREIGN PATENT DOCUMENTS

GB 2576304 A 2/2020
GB 2589490 A 6/2021
(Continued)

OTHER PUBLICATIONS

Stewart et al., A Content-Addressable DNA Database with Learned Sequence Encodings, 2018, in DNA Computing and Molecular Programming: 24th International Conference, DNA 24, Doty and Dietz (eds.), Springer Nature Switzerland, pp. 55-70 (Year: 2018).*
(Continued)

*Primary Examiner* — Jesse P Frumkin
*Assistant Examiner* — Theodore Charles Striegel
(74) *Attorney, Agent, or Firm* — Klarquist Sparkman, LLP

(57) ABSTRACT

Multiplex similarity search can be performed in a DNA data storage context. The described technologies can support a plurality of different DNA data storage queries in a single query run. A linking strand can be used to connect a query to its matching data element. After the query finds a matching data element, a result strand can be sequenced to the reveal the matching data element as well as which of the queries resulted in the match. Thus, in a multiplex similarity search scenario, a plurality of result strands from a single query run can be correlated to a plurality of different queries. Also, the result strand can be of significantly longer length than both the unmatched data strands and the unmatched query strands. Therefore, filtering based on length can provide more accurate results.

20 Claims, 38 Drawing Sheets

(51) Int. Cl.
  G16B 45/00 (2019.01)
  G16B 50/30 (2019.01)

(56) References Cited

U.S. PATENT DOCUMENTS

| | | | |
|---|---|---|---|
| 2017/0141793 | A1 | 5/2017 | Strauss et al. |
| 2018/0223340 | A1 | 8/2018 | Chen et al. |
| 2018/0223341 | A1 | 8/2018 | Chen et al. |
| 2018/0230509 | A1 | 8/2018 | Chen et al. |
| 2018/0253528 | A1 | 9/2018 | Strauss et al. |
| 2018/0265921 | A1 | 9/2018 | Chen et al. |

FOREIGN PATENT DOCUMENTS

| | | |
|---|---|---|
| WO | WO 2018/102064 | 6/2018 |
| WO | 2020/239806 | 3/2020 |

OTHER PUBLICATIONS

Reif et al., Application of Biomolecular Computing to Medical Science: a Biomolecular Database System for Storage, Processing, and Retrieval of Genetic Information and Material, 2006, in Complex Systems Science in Biomedicine, Deiboeck and Kresh, (eds.), Springer Inc., pp. 701-735 (Year: 2006).*
Tsaftaris et al., Retrieval Efficiency of DNA-Based Databases of Digital Signals, Sep. 2009, IEEE Transactions on Nanobioscience 8(3): 259-270 (Year: 2009).*
Killoran et al., Generating and designing DNA with deep generative models, Dec. 2017, arXiv 1712.06148, pp. 1-19 (Year: 2017).*
Yin et al., Programming biomolecular self-assembly pathways, Jan. 2008, Nature 451(7176): 318-322 (Year: 2008).*
Zhang et al., A DNA-Origami Chip Platform for Label-Free SNP Genotyping Using Toehold-Mediated Strand Displacement, Aug. 2010, Small 6(17): 1854-1858 (Year: 2010).*
Leray et al., Effectiveness of Annealing Blocking Primers versus Restriction Enzymes for Characterization of Generalist Diets: Unexpected Prey Revealed in the Gut Contents of Two Coral Reef Fish Species, Apr. 2013, PLoS ONE 8(4): Article e58076, pp. 1-11 (Year: 2013).*
Liu et al., Development of a Blocking Primer to Inhibit the PCR Amplification of the 18S rDNA Sequences of Litopenaeus vannamei and Its Efficacy in Crassostrea hongkongensis, Apr. 2019, Frontiers in Microbiology 10: Article 830, pp. 1-15 (Year: 2019).*
Loh, Anchored PCR: Amplification with single-sided specificity, Feb. 1991, Methods 2(1): 11-19 (Year: 1991).*
Bornholt et al., A DNA-Based Archival Storage System, Mar. 2016, Proceedings of ASPLOS '16, pp. 637-649, Association for Computing Machinery (Year: 2016).*
Bornholt et al., Toward a DNA-based Archival Storage System, Jun. 2017, IEEE Micro 37(3): 98-104 (Year: 2017).*
"Short Hairpin RNA," Wikipedia, visited May 6, 2019, 4 pages.
"DNA digital data storage," Wikipedia, visited May 6, 2019, 6 pages.
Stewart et al., "A Content-Addressable DNA Database with Learned Sequence Encodings," 24th International Conference on DNA Computing and Molecular Programming, Oct. 2018, 16 pages.
Adleman, L.M, "Molecular computation of solutions to combinatorial problems," Science 266(5187), 1021-1024 (1994).
Andoni, A., Indyk, P, "Near-optimal hashing algorithms for approximate nearest neighbor in high dimensions," Communications of the ACM 51(1), 117-122 (2008).
Baum, E.B., "Building an associative memory vastly larger than the brain," Science 268(5210), 583-585 (1995).
Church et al., "Next-generation digital information storage in DNA," Science 337(6102), 1628-1628 (2012).
Dirks et al., "Thermodynamic analysis of interacting nucleic acid strands," SIAM Review (2007).
Erlich et al., "DNA Fountain enables a robust and efficient storage architecture," Science 355(6328), 950-954 (2017).
Garzon et al., "Efficiency and reliability of semantic retrieval in DNA-based memories," DNA 2943 (Chapter 15), 157-169 (2003).
Goldman et al., "Towards practical, high-capacity, low-maintenance information storage in synthesized DNA," Nature 494(7435), 77-80 (2013).
Grass et al., "Robust chemical preservation of digital information on DNA in silica with error-correcting codes," Angewandte Chemie Intl. Edition 54(8), 2552-2555 (2015).
Griffin et al., "Caltech-256 object category dataset," Tech. rep., California Institute of Technology (2007).
IDC: Where in the world is storage (2013), http://www.idc.com/downloads/where_is_storage_infographic_243338.pdf.
Indyk, et al., "Approximate nearest neighbors: Towards removing the curse of dimensionality," In: Proceedings of the Thirtieth Annual ACM Symposium on Theory of Computing. pp. 604-613. STOC '98, ACM, New York, NY, USA (1998). https://doi.org/10.1145/276698.276876.
Kawashimo et al., "Dynamic neighborhood searches for thermodynamically designing DNA sequence," DNA Computing pp. 130-139 (2007).
Lee et al. "Similarity search on automata processors," In: 2017 IEEE International Parallel and Distributed Processing Symposium (IPDPS). pp. 523-534 (2017).
Li, H, "Aligning sequence reads, clone sequences and assembly contigs with BWA-MEM," (2013), 3 pages.
Neel, A., Garzon, M., "Semantic Retrieval in DNA-Based Memories with Gibbs Energy Models," *Biotechnology Progress* 22(1), 86-90 (2006), 5 pages.
Neel et al., "Soundness and quality of semantic retrieval in DNA-based memories with abiotic data," *2004 Congress on Evolutionary Computation*, pp. 1889-1895. IEEE (2004), 7 p.
Organick, et al., "Random access in large-scale DNA data storage," Nature Biotechnology 36(3), 242-248 (Mar. 6, 2018), 9 pages.
Reif, et al., "Computationally inspired biotechnologies: Improved DNA synthesis and associative search using error-correcting codes and vector-quantization?" In: Condon, A., Rozenberg, G. (eds.) *DNA Computing*. pp. 145-172. Springer Berlin Heidelberg, Berlin, Heidelberg (2001).
Reif, et al., "Experimental Construction of Very Large Scale DNA Databases with Associative Search Capability," In: Jonoska, N., Seeman, N.C. (eds.) *DNA Computing*. pp. 231-247. Springer Berlin Heidelberg, Berlin, Heidelberg (2002).
Salakhutdinov et al., "Semantic hashing," International Journal of Approximate Reasoning 50(7), 969-978 (2009).
Tsaftaris et al., "DNA hybridization as a similarity criterion for querying digital signals stored in DNA databases," In: 2006 IEEE International Conference on Acoustics Speed and Signal Processing. pp. II-1084-II-1087. IEEE (2006), 4 pages.
Tsaftaris et al., "DNA-based matching of digital signals," In: 2004 IEEE International Conference on Acoustics, Speech, and Signal Processing. pp. V-581-4. IEEE (2004), 4 pages.
Tulpan et al., "Thermodynamically based DNA strand design," Nucleic Acids Research 33(15), 4951-4964 (2005).
Wan et al., Deep learning for content-based image retrieval: A comprehensive study pp. 157-166 (2014). https://doi.org/10.1145/2647868.2654948.
Weiss et al., "Spectral hashing," In: Proceedings of the 21st International Conference on Neural Information Processing Systems. pp. 1753-1760. NIPS'08, Curran Associates Inc., USA (2008).
Wu et al., "Continuously tunable nucleic acid hybridization probes," Nature Methods 12(12), 1191-1196 (2015).
Yazdi et al., "Portable and Error-Free DNA-Based Data Storage," Scientific Reports 7(1), 1433 (2017).
Zadeh et al., "NUPACK: Analysis and design of nucleic acid systems," Journal of Computational Chemistry 32(1), 170-173 (2011).
Zhang et al., "Optimizing the specificity of nucleic acid hybridization," Nature Chemistry 4(3), 208-214 (2012).
Ceze et al., "Molecular Digital Data Storage Using DNA", In Journal of Nature Reviews Genetics, vol. 20, Issue 8, May 8, 2019, 11 Pages.

(56) References Cited

OTHER PUBLICATIONS

Stewart et al., "Slides for a Content-Addressable DNA Database with Learned Sequence Encodings", Retrieved from: https://pdfs.semanticscholar.org/7eb1/fbda70aea2a0b7accbb09ad997465044f519.pdf, Oct. 8, 2018, pp. 1-63.

"International Search Report and Written Opinion Issued in PCT Application No. PCT/US20/037680," Mailed Date: Sep. 21, 2020, 13 Pages.

"Notice of Allowance Issued in European Patent Application No. 20735780.7", Mailed Date: Feb. 21, 2023, 8 Pages.

"Notice of Allowance Issued in European Patent Application No. 20735780.7", Mailed Date: Jun. 15, 2023, 2 Pages.

Communication under Rule 71(3) EPC, Intention to Grant, received in counterpart European Application No. 20735780.7 -1126, dated Feb. 21, 2023, 8 pages.

\* cited by examiner

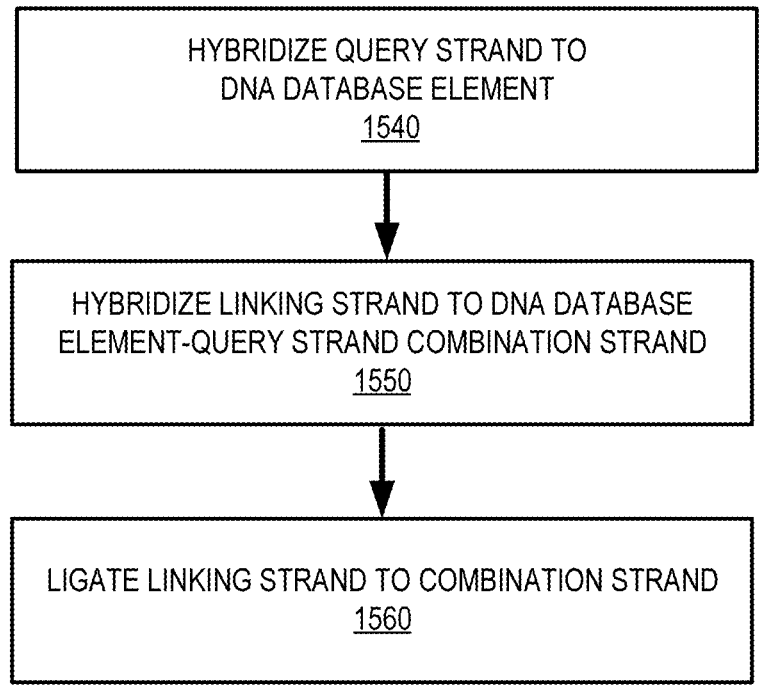
FIG. 15

1900

FIG. 20

FIG. 27A Database Element Design

FIG. 27B Query Design

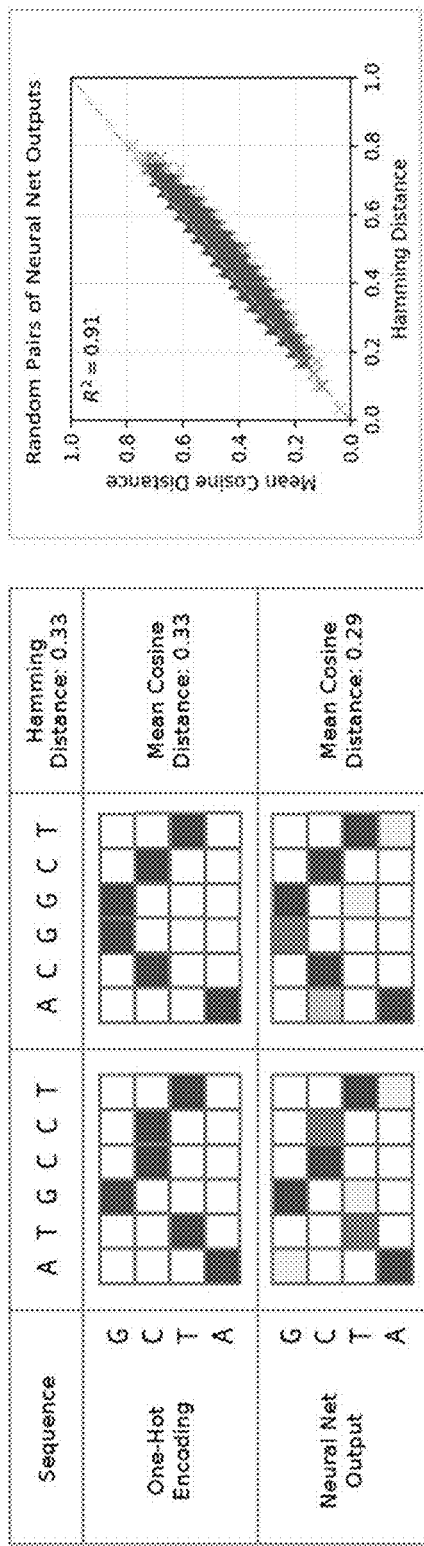
FIG. 30A COMPARISON OF SEQUENCE REPRESENTATIONS AND ASSOCIATED DISTANCE METRICS
FIG. 30B EFFECTIVENESS OF NEURAL NETWORK OUTPUT

| Layer Type | Diagram | Dimensionality |
|---|---|---|
| Sequence | A T G ... C C T | 30 x 1 |
| ReLU + Softmax "One-Hot" Output | | 30 x 4 |
| Fully Connected | | 10 x 128 x 30 x 4 |
| ReLU Activation | | 10 x 128 |
| Convolution 2 | | 1 x 128 x 128 |
| Sine Activation | | 10 x 128 |
| Convolutional 1 | | 1 x 128 |
| Input (VGG16+PCA) | | 10 x 1 |

FIG. 32

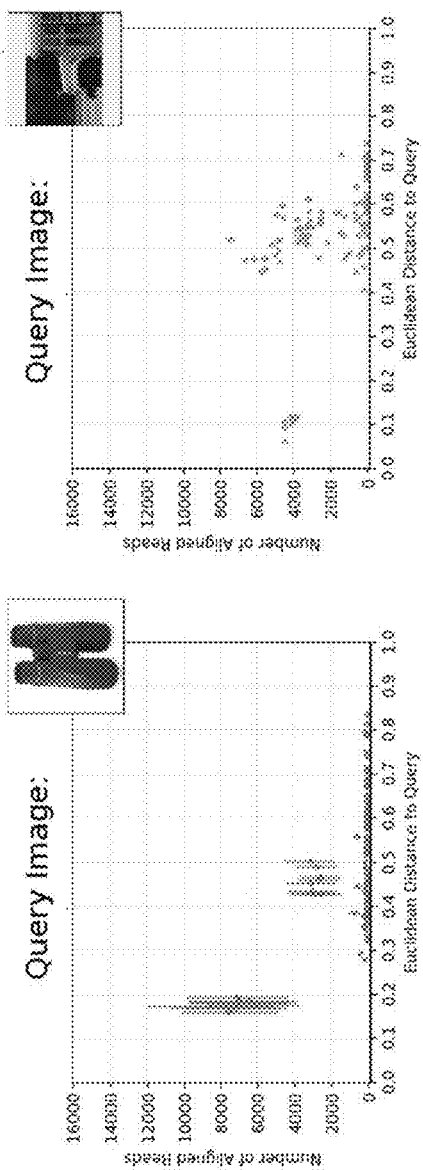
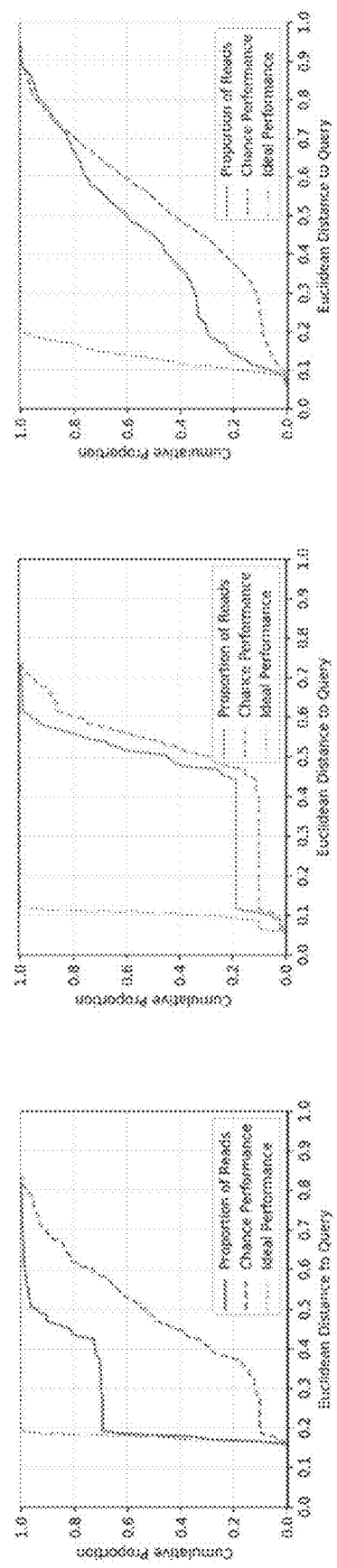
FIG. 35A
FIG. 35B

MULTIPLEX SIMILARITY SEARCH IN DNA DATA STORAGE

FIELD

The field generally relates to searching a DNA data storage database.

BACKGROUND

The volume of digital information is increasing at an exponential rate. This vast increase in the amount of digital information may outpace the ability of conventional storage technologies. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, created synthetic DNA encoding that string, sequenced the synthetic DNA, and then recovered the original computer file with 100% accuracy.

However, while amazing strides have been made in the field, there still remains room for improvement.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a method comprises, in a single multiplex similarity search query reaction run comprising a plurality of DNA database elements implementing DNA data storage, matching a query strand to a DNA database element, wherein the matching comprises hybridizing a feature nucleotide sequence of the DNA database element to a complementary feature nucleotide sequence of the query strand, and the matching comprises arranging a DNA linking strand into a connection between a data strand of the DNA database element and the query strand, wherein the arranging produces a DNA result element comprising a result strand comprising the query strand and the data strand; sequencing the result strand comprising the query strand and the data strand, wherein the sequencing yields a digital representation of an identifier region of the query strand and a digital representation of an identifier region of the data strand of the matched DNA database element, thereby indicating a digital query and a digital data item matching the digital query; wherein the single multiplex similarity search query reaction run comprises matching query strands having different complementary feature nucleotide sequences to different DNA database elements.

In another embodiment, a DNA database comprises a collection of DNA database elements representing respective digital database items; and a collection of query strands representing respective queries targeting the digital database items via different reverse complementary query sequences; wherein at least one of the DNA database elements and at least one of the query strands are connected via a DNA linking strand, whereby multiplex similarity search in DNA data storage is performed.

In another embodiment, one or more non-transitory computer-readable media comprise computer-executable instructions capable of converting digital data items to sequences for data strands of DNA database elements; computer-executable instructions capable of converting a plurality of digital queries to a plurality of respective sequences for query strands; computer-executable instructions capable of receiving result strand sequences generated by a completed query reaction run performed with the DNA database elements and the query strands; and computer-executable instructions capable of decoding the result strand sequences into digital query results, wherein the digital query results indicate which digital data items matched which of the plurality of digital queries.

The foregoing and other objects, features, and advantages will become more apparent from the following detailed description, which proceeds with reference to the accompanying figures.

BRIEF DESCRIPTION OF THE DRAWINGS

FIG. 15 is a flowchart of an example linking-strand-late method of generating a result strand for multiplex similarity search in DNA data storage.

FIG. 20 is a block diagram of an example unwound result stand for multiplex similarity search in DNA data storage.

FIGS. 30A and 30B show one-hot sequence encodings and their properties.

FIG. 32 is a diagram of a neural network architecture for a sequence encoder.

FIGS. 35A and 35B are diagrams showing number of aligned reads and cumulative distribution of aligned reads.

DETAILED DESCRIPTION

Example 1—Overview

Figure 1:
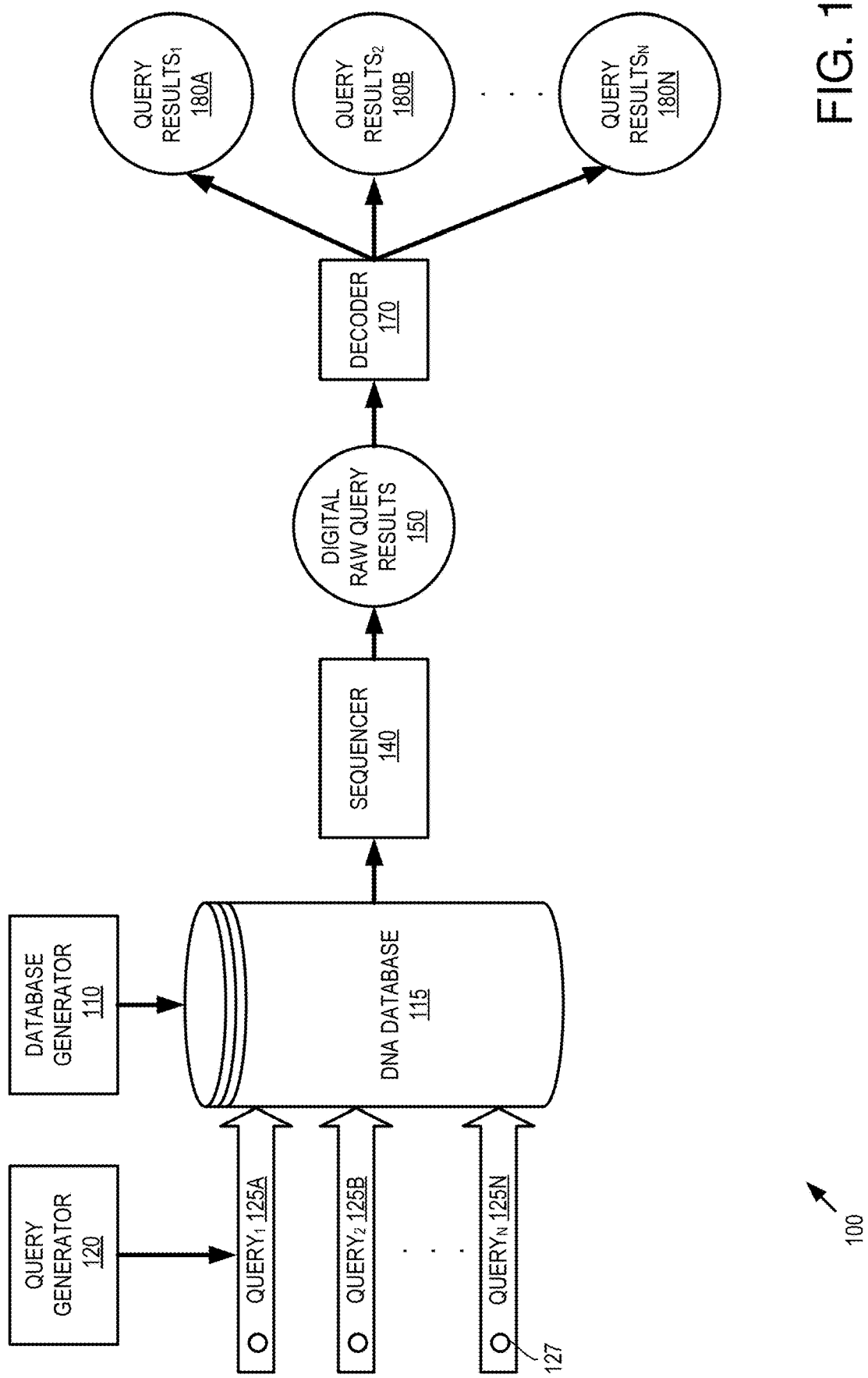
FIG. 1 is a block diagram of an example system implementing multiplex similarity search in a DNA data storage context.

Key-based random-access techniques for retrieval of data in a DNA storage context does not provide full database functionality. For example, similarity search is lacking from a strict key-based technique. Similarity search involves content-based searching. In other words, searching can include a query on the content of target items rather than on a key that is not considered part of the content. The difference is significant because searching can be performed on items having a content relationship to the search, where such relationship may not yet be represented or stored. So, a matching item can be discovered by the search, rather than fetched by a known key.

Similarity search can be achieved in a DNA storage context, but it can be limited to performing search with a single query during a query run. Such an approach is called "single-plex" similarity searching herein. The multiplex similarity search technologies described herein can offer significant advantages over single-plex similarity searching, including saving on both time and resources.

Further, the described technologies can result in query results that are physically longer than other strands present during a reaction. The length of the strands can thus be used to differentiate over other strands, leading to increased accuracy, whether in a multiplex similarity search or other context.

The described technologies thus offer considerable improvements over conventional DNA storage search techniques.

Overall, the technologies relate to data retrieval and search from DNA-based archival data storage. The technologies can achieve multiple queries in one single reaction. In addition, the technologies make the captured item longer than the non-captured ones, which allows another size selection to achieve better accuracy.

The technologies can link a DNA query to its selected data item. This can be done in different ways. For example, by ligating an additional DNA linking strand to the pair of DNA query and the selected DNA data strand, or by synthesizing a DNA query strand with a dummy linking strand. After a DNA query binds to its DNA data strand, a ligation reaction can be performed to link the two DNA strands.

The technologies can be applied to a number of use cases involving data storage and retrieval. For example, general database operations, cloud archival data storage services, collaborative filtering, and the like can be improved by application of the technologies describe herein.

Example 2—Example Terminology

The term "primer" as used herein refers to an oligonucleotide which is capable of acting as a point of initiation of nucleic acid synthesis when placed under conditions in which synthesis of a primer product, which is complementary to a nucleic acid strand, is induced, e.g., in the presence of four different nucleotide triphosphates with appropriate enzymes at a suitable temperature and salt concentration. Specific length and sequence will depend on the complexity of the required primer targets, as well as on the conditions of primer use such as temperature and ionic strength. In some implementations, a primer can be 5-50 nt, 10-25 nt, or 15-20 nt in length. The fact that amplification primers do not have to match exactly with the corresponding template sequence to warrant proper amplification is amply documented in the literature. It is generally accepted that a typical length of PCR primers is 18-22 nt. This length is long enough for adequate specificity and short enough for primers to bind easily to the template at the annealing temperature.

Polynucleotides such as DNA and ribonucleic acid (RNA), including polynucleotides that have unnatural bases, may be used to store digital information by designing a sequence of nucleotide bases that encodes the zeros and ones of the digital information. There are various techniques and encoding schemes for using nucleotide bases to represent digital information. See e.g., Grass et al., "Robust Chemical Preservation of Digital Information on DNA in Silica with Error-Correcting Codes," 54 *Angew. Chem. Int. Ed.* 2552

(2015) and Organick et al., "Random access in large-scale DNA data storage," 36:3 Nat. Biotech. 243 (2018). Advantages of using DNA rather than another storage media for storing digital information include information density and longevity. The DNA storage structure and methods described in this disclosure can improve information density, longevity, and accessibility relative to other techniques for storing DNA. The contents of the disclosure may be used with any type of polynucleotide such as DNA, RNA, and DNA-RNA hybrids, thus references to "DNA" are illustrative and not intended to limit the application to only DNA or to only use of natural nucleotide bases.

Naturally occurring DNA strands consist of four types of nucleotides: adenine (A), cytosine (C), guanine (G), and thymine (T). A DNA strand, or polynucleotide, is a linear sequence of these nucleotides. The two ends of a DNA strand, referred to as the 5' and 3' ends, are chemically different. DNA sequences are conventionally represented starting with the 5' nucleotide end at the left. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus the two sequences are the reverse complement of each other. Two strands do not need to be fully complementary to bind to one another. Ribonucleic acid (RNA) has a similar structure to DNA and naturally occurring RNA consists of the four nucleotides A, C, G, and uracil (U) instead of T. Discussions in this disclosure mention DNA for the sake of brevity and readability, but RNA may be used in place of or in combination with DNA. RNA may also bind to DNA forming a hybrid molecule.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

"Hybridizing" as used herein means placing two complementary single-strand (ss) (or partially single-strand) DNA strands in conditions that allow hybridization to form a double-strand (ds) DNA strand or causing two complementary ssDNA strands to hybridize and form a dsDNA strand. Hybridization may be performed under high stringency conditions.

Artificial synthesis of DNA allows for creation of DNA strands with arbitrary series of the nucleotides. The order in which individual monomers of these four nucleotides are assembled together into a polymer can represent information in an analogous manner as 0 and 1 in digital computers. Thus, multiple DNA strands can be synthesized with particular orders of the four DNA nucleotides and encode large amounts of information. The information is encoded as a series of DNA nucleotides, but may represent any type of data such as text, audio files, video files, or anything else that may be encoded by conventional binary data recording in electronic computers.

The term "amplifying" which typically refers to an exponential increase in the number of copies of the target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including polymerases and thermostable polymerases such as DNA polymerase, RNA polymerase and reverse transcriptase, aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art.

One technique for amplification is PCR which may use a PCR thermocycler. A variety of PCR techniques are known and can be used with the techniques described herein. PCR techniques are typically used for the amplification of at least a portion of an oligonucleotide. The sample to be tested for the presence of an analyte-specific sequence is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

The entire contents of a DNA pool, or other vessel containing the DNA to be analyzed, may be placed in a PCR thermocycler. The process of PCR is well-known to those skilled in the art and has been extensively characterized. PCR involves the following three steps: denaturation, annealing, and extension. First, any dsDNA is denatured, converting to single strands. The primers are then annealed to the complementary regions of the single stranded molecules. In the third step, the primers are extended by the action of the DNA polymerase. All these steps are temperature sensitive and a common choice of temperatures is 94° C., 60° C., and 70° C., respectively. In order to amplify the sequencing adaptors together with the designated DNA, the primers are designed to hybridize with the ends of the sequencing adaptors in order to create multiple copies of the ligation products. Melting Temperature ($T_m$) by definition is the temperature at which one half of a DNA duplex will dissociate to become single stranded and indicates the duplex stability. Primers with melting temperatures in the range of 52-58° C. generally produce the best results. Primers with melting temperatures above 65° C. have a tendency for secondary annealing. The GC content of the sequence gives a fair indication of the primer $T_m$. Other DNA strands from the DNA pool will still be present during PCR, but primers present in the PCR mix will be unlikely to hybridize with those DNA strands. The selectively amplified DNA generated by the PCR thermocycler may be provided to a DNA sequencer. PCR amplification prior to sequencing improves the yield and may convert ssDNA to dsDNA which improves the stability and longevity of DNA in storage.

Example 3—Example System Implementing Multiplex Similarity Search in a DNA Data Storage Context FIG. 1 is a block diagram of an example system 100 implementing multiplex similarity search in a DNA data storage context. In the example, the system 100 can include a database generator 110 that generates a DNA database 115.

As described herein, the DNA database 115 can comprise data strands that take the form of strands of DNA constructed to represent respective data items.

A query generator 120 can generate a plurality of queries 125A-N. As described herein, the queries 125A-N can comprise query strands that take the form of strands of DNA constructed to represent respective queries. Although single query strands are shown, in practice, many copies of the respective query strands 125A-N can be included in a single reaction run.

The queries 125A-N can be carefully constructed to be partially complementary to the data strands in a way that results in similarity search via reaction between a query strand and a matching data strand in the DNA database 115. In practice, many concurrent reactions between strands can occur in parallel in a single reaction run, both for a single query and across queries. Notably, in the multiplex similarity search technology described herein, multiple queries 112A-N can be included in a single reaction run, and the multiple queries 112A-N can yield respective separate results 180A-N for the multiple queries 112A-N. As described herein, a linking strand 127 can be included in the query, allowing the resulting reaction strand to be traced back to the query from which it originated by linking a query strand to its matching data strand.

The result strands that are yielded during a reaction run can be read by the sequencer 140 and are output as digital raw query results 150 (e.g., digital representations of the result strands).

A decoder 170 can then process the digital raw query results 150 to yield query results 180A-N, which are digital query results for respective of the queries 125A. For example, query results 180A indicate the data items that match the query 125A, and so on.

In practice, the systems shown herein, such as system 100, can vary in complexity, with additional functionality, more complex components, and the like. For the digital aspects, additional components can be included to implement security, redundancy, load balancing, report design, and the like.

The described computing systems can be networked via wired or wireless network connections, including the Internet. Alternatively, systems can be connected through an intranet connection (e.g., in a corporate environment, government environment, or the like).

The system 100 and any of the other systems described herein can be implemented in conjunction with any of the hardware components described herein, such as the computing systems described below (e.g., processing units, memory, and the like). In any of the examples herein, the data items, digital query results, and the like can be stored in one or more computer-readable storage media or computer-readable storage devices. The technologies described herein can be generic to the specifics of operating systems or hardware and can be applied in any variety of environments to take advantage of the described features.

Figure 2:
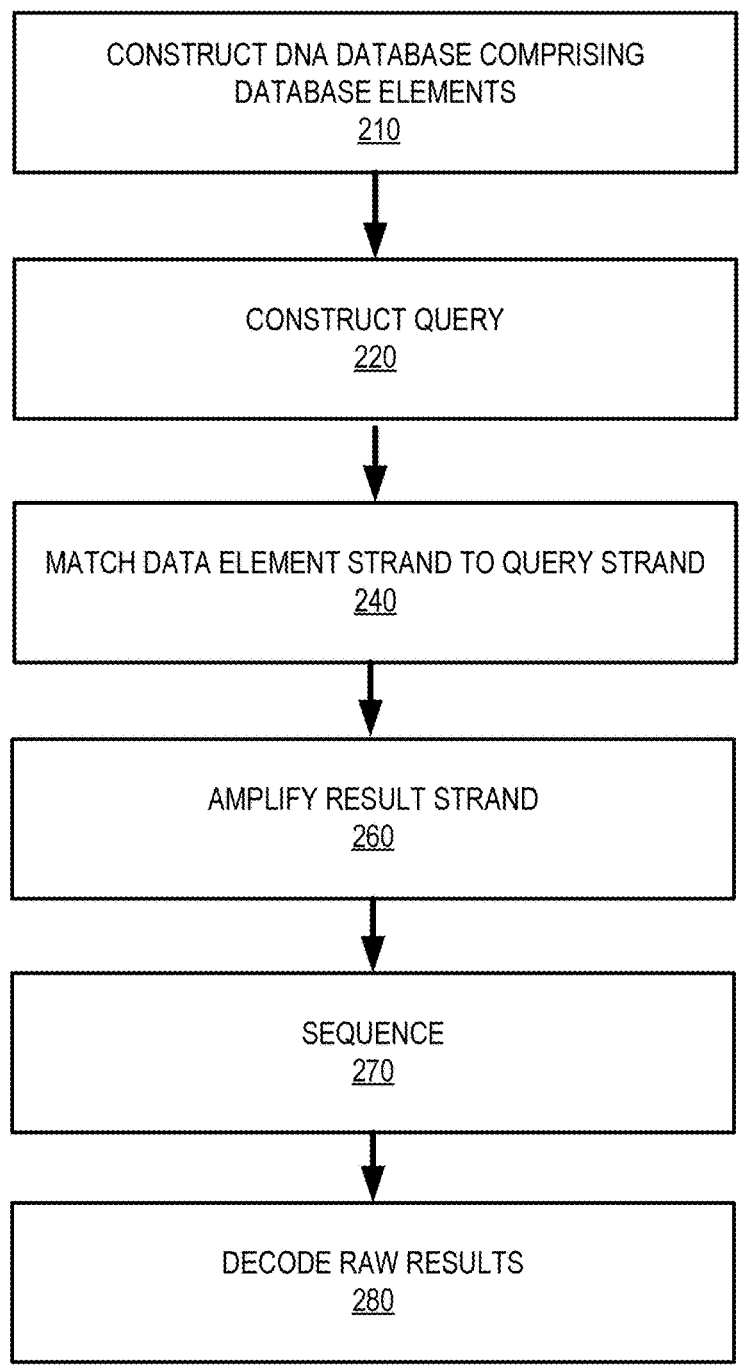
FIG. 2 is a flowchart of an example method of multiplex similarity search in a DNA data storage context.

Example 4—Example Method Implementing Multiplex Similarity Search in a DNA Data Storage Context FIG. 2 is a flowchart of an example method 200 of multiplex similarity search in a DNA data storage context and can be performed, for example, by the system of FIG. 1.

At 210, a DNA database comprising DNA database elements (e.g., with data strands as described herein) are constructed. As described herein, a digital data item can be converted into a DNA representation of the digital data item. The construction process can be repeated for different digital data items, and quantities of the DNA database elements can be mixed together to populate the DNA database with a plurality of DNA database elements representing respective, different digital data items.

At 220, DNA representations of a digital query (e.g., a query strand) are constructed. As described herein, a query for digital data items can be converted into a DNA representation of the query. The construction process can be repeated for different digital queries. Although not required, the query strands can be mixed together to form a query strand mixture.

At 240, a DNA database element is matched to a query strand in a single multiplex similarity search query reaction run. The run can comprise a plurality of DNA database elements implementing DNA data storage. A chemical reaction binds the query strand to those DNA database element strands that are similar as described herein. Thus, the matching comprises hybridizing a feature nucleotide sequence of a DNA database element to a complementary feature nucleotide sequence of the DNA query strand. In practice, query strands of a single query can match a plurality of different data strands representing different digital items (e.g., more than one data item is similar to the query). Further, as described herein, multiplex similarity search can involve more than one query at a time (e.g., per single reaction run); therefore, DNA database elements can be matched to query strands representing different digital queries. In some cases, more than one query strand (e.g., representing different digital queries) can match multiple DNA database elements representing a same digital data item. In a multiplex search scenario, there can be more than one result (e.g., plural result strands for plural, different query strands representing different digital queries).

As described herein, the matching process can include arranging a DNA linking strand into a connection between a DNA data strand of the DNA database element and the DNA query strand, producing a DNA result element comprising a DNA result strand comprising the DNA query strand and the DNA data strand. Completing the connection can comprise performing one or more ligation reactions as described herein.

At 260, the yielded result strand can be amplified. In a multiplex scenario, multiple result strands can be amplified. A double-stranded result element (e.g., comprising a result strand) can be amplified using forward and reverse primers to achieve exponential amplification. Or, a single-stranded result strand can be amplified using either a forward primer or a reverse primer, leading to linear amplification.

At 270, the result strands can be sequenced by a sequencer to convert the result strands into digital representations, yielding raw results of the query reaction run. The result strand comprises the query strand and the data strand. The sequencing thus yields a digital representation of an identifier region of the query strand (e.g., f(Q)*) and a digital representation of an identifier region of the data strand (e.g., d(T)) of the matched DNA database element. The result strand can thereby indicate a digital query and a digital data item matching the digital query (e.g., a digital data item that is at least similar to the feature value specified in the digital query) by virtue of the fact that f(Q)* and d(T) appear on the same strand (e.g., connected by the linking strand).

At 280, the raw results can be decoded, yielding query results showing which digital data items matched which digital item queries.

After sequencing the result strand, the digital representation of the identifier region of the query strand can be mapped to a digital query for which the query strand was created. The digital query can then be indicated (e.g., the results can be separated out by digital query).

In a multiplex reaction, there is more than one query. So, for at least one other result strand, a digital representation of the identifier of the query strand can be mapped to a different query strand (e.g., that was created for a different digital query). Thus, digital representations of identifier regions of query strands can be mapped to respective digital queries for which the query strands were created.

In a multiplex reaction, the sequencing generates results for a plurality of result strands representing a plurality of digital queries. Results of the result strands can be separated by digital query. For example, a first set of underlying digital data items (e.g., or their identifiers) that are indicated as matching a first digital query (e.g., by virtue of appearing on the same result strand) can be associated with (e.g., indicated as matching) the first digital query, and a second set of underlying digital data items (e.g., or their identifiers) that are indicated as matching a second digital query (e.g., by virtue of appearing on the same result strand) can be associated with (e.g., indicated as matching) the second query. An indication of matching can be stored so that the results can be presented or processed further (e.g., the process accepts a plurality queries as input and indicates sets of data items that matched the queries, and the results are separated out by query).

As described herein, the multiplex similarity search query reaction run can comprise matching query strands having different complementary feature nucleotide sequences (e.g., representing queries for different features) to different DNA database elements. A plurality of the different DNA database elements can represent respective, different underlying digital data items.

As described herein, the query strands can have different complementary nucleotide sequences that represent respective, different digital queries. For the different queries, which of the digital data items represented in the query reaction run match the respective, different digital queries can be identified. Such identifying can comprise, for a given result strand, identifying an address of a digital data item encoded on the given result strand (e.g., in the data strand portion) and identifying a query identifier encoded on the given result strand (e.g., in the query strand portion).

In practice, the acts shown can be performed by different actors at different times. For example, the DNA database can be constructed ahead of time and maintained for queries at a later date. Similarly, the query strands can be constructed ahead of time, predetermined query mixtures can be stored, and so forth. The technologies described herein are not limited to such scenarios but can be applied to any use case in which multiplex similarity search in DNA data storage is desired.

Example 5—Example System Creating a DNA Database

Figure 3:
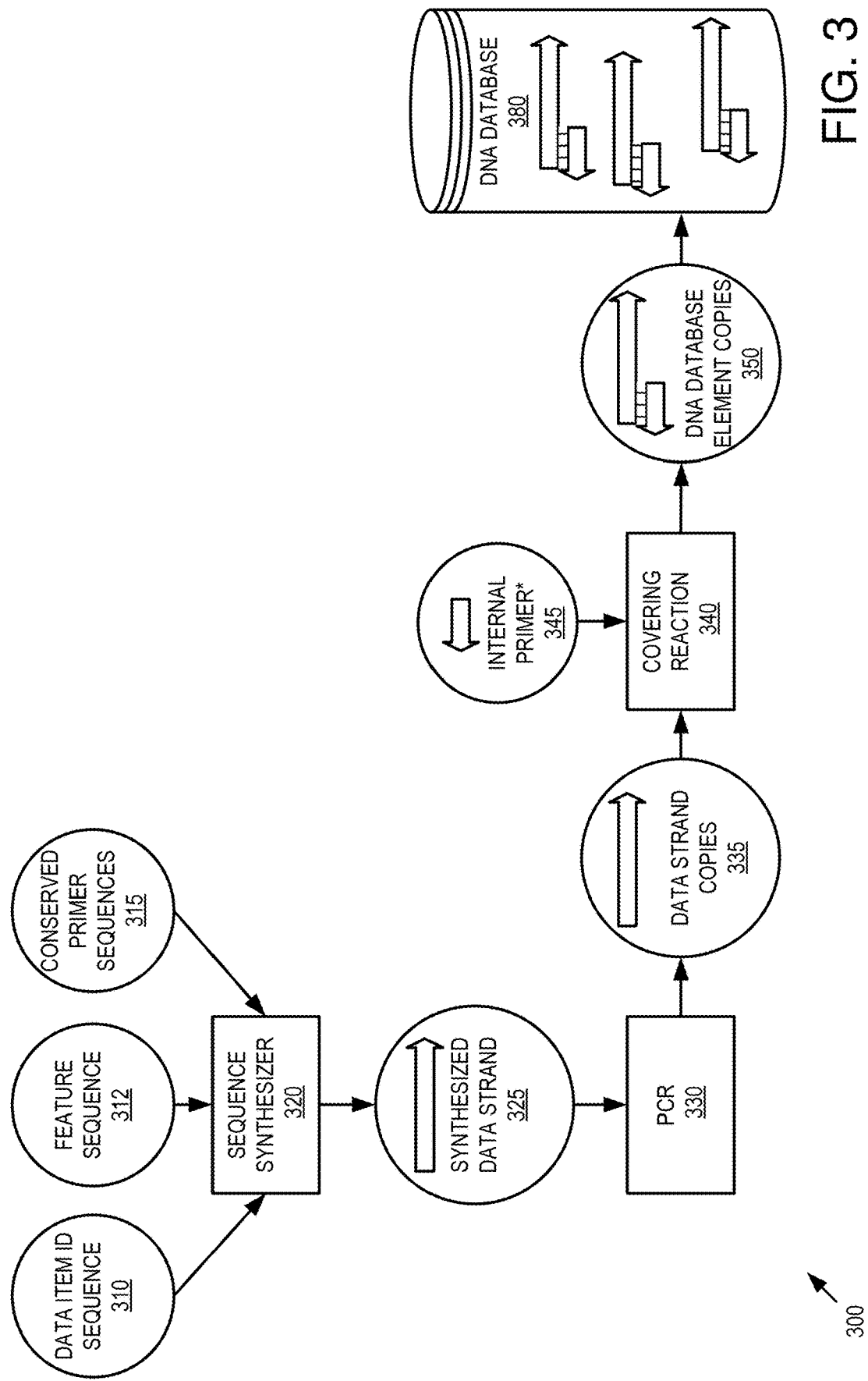
FIG. 3 is a block diagram of an example system creating a DNA database for multiplex similarity search in DNA data storage.

FIG. 3 is a block diagram of an example system 300 creating a DNA database 380 for multiplex similarity search in DNA data storage that can be used in any of the examples herein. Although DNA database elements and data strands for a single digital data item are sometimes described herein, in practice, the DNA database 380 can contain DNA database elements for a plurality of digital data items. For example, the system 300 can be re-used or run in parallel for more digital data items, generating more DNA database element copies (e.g., for different digital data items).

The sequence synthesizer 320 accepts the data item identifier sequence 310, feature sequence 312, and conserved primer sequences 315 as input and generates a synthesized data strand 325 (e.g., an oligonucleotide). In practice, the inputs can be concatenated to result in a single sequence that is generated by the synthesizer 320.

The data item identifier sequence 310 is a unique sequence (e.g., within data items) that identifies the underlying digital data item that has a feature represented by the feature sequence 312. A mapping between data item identifier sequences 310 and underlying digital data items can be maintained that allows retrieval of the digital data item represented by the data item identifier sequence 310, whether it is stored digitally or in DNA (or both).

The synthesized data strand 325 can be amplified (e.g., enriched) to many copies 335 via a PCR reaction 330.

Alternatively, or additionally, multiple data strands can be synthesized instead of or in addition to using the PCR technique.

A covering reaction 340 can use an oligonucleotide 345 complementary to an internal primer with single-step PCR to cover portions of the data strand as described herein. The reaction 340 results in DNA database element copies 350 that then can be incorporated into the DNA database 380 for use in multiplex similarity search in DNA data storage.

Example 6—Example Method of Creating a DNA Database

Figure 4:
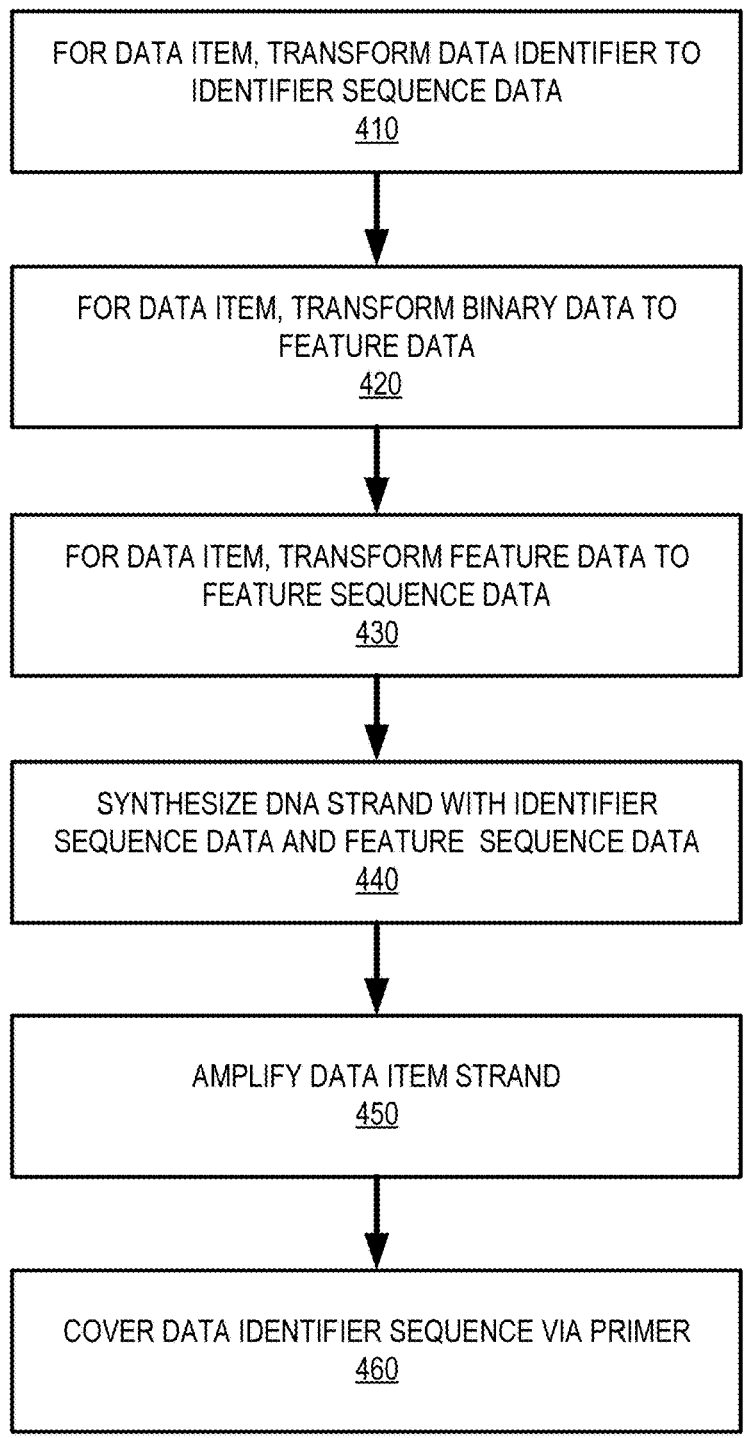
FIG. 4 is a flowchart of an example method of creating a DNA database for multiplex similarity search in DNA data storage.

FIG. 4 is a flowchart of an example method 400 of creating a DNA database for multiplex similarity search in DNA data storage that can be used in any of the examples herein and can be performed, for example, by the system of FIG. 3. As described herein, the process can be repeated and/or executed in parallel for multiple digital data items.

At 410, for a given digital data item, the digital data item identifier is transformed to identifier sequence data (e.g., a digital string of nucleotides representing a part of an oligonucleotide to be synthesized). In practice, such sequence data can be pre-computed so that a ready list of identifiers is already available. The sequence data may be trivial (e.g., it merely needs to function as a unique identifier); however, some transformation is typically performed (e.g., to represent the identifier in a one-hot or other representation technique).

At 420, the binary data of one or more digital features of the digital data item is transformed to digital feature data. Then, at 430, the digital feature data is transformed to a feature sequence. Such a sequence can take the form of a digital representation of an oligonucleotide representing one or more digital features of the digital data item. As described herein, such a representation can be formulated so that binding to queries representing similar (e.g., including same) features is encouraged.

At 440, a DNA strand (e.g., oligonucleotide) is synthesized with the identifier sequence data and the feature sequence data. Conserved primers (e.g., primers used across data strands for different digital data items as described herein) can be included in the process.

The underlying digital data item represented can be any form of digital data, such as text, audio, image, video, or anything else that can be encoded by digital (e.g., binary)

data recording in electronic computing systems. In practice, the data item can be identified in a data strand by its identifier (e.g., itself a binary value) that maps to the underlying digital data item.

At 450, the preliminary data strand is amplified. An exponential PCR can be performed first to enrich the data strands. Then, a linear PCR can be performed to create single-stranded oligonucleotides by using forward primers.

At 460, the data identifier sequence is covered via a primer in a single-step PCR technique as described herein. Covering the identifier sequence prevents the identifier region from interfering with the matching process during hybridization as described herein.

The method 400 results in a large number of copies of the data strand which can be used in combination with the query strands described herein to achieve multiplex similarity search in DNA data storage.

Example 7—Example DNA Database Element

Figure 5:
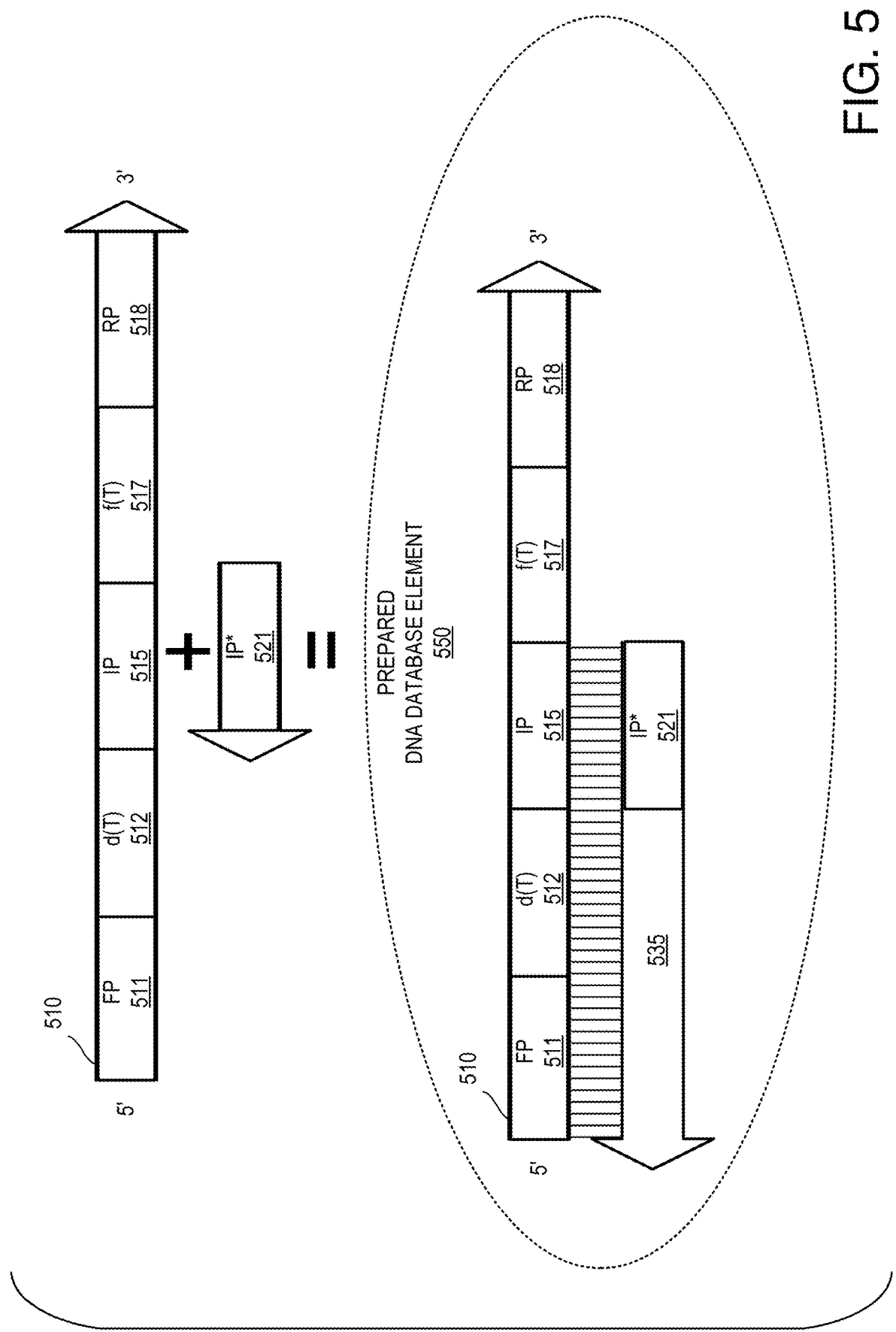
FIG. 5 is a block diagram of an example DNA database element for multiplex similarity search in DNA data storage.

FIG. 5 is a block diagram of an example DNA database element for multiplex similarity search in DNA data storage that can be used in any of the examples herein.

A DNA data strand 510 can take the form of an oligonucleotide formed as a sequence of nucleotides that make up a molecule. For sake of simplicity, a DNA data strand is sometimes called a "data strand" herein. The DNA data strand 510 can take the form of an oligonucleotide. As described herein, the data strand 510 can represent a respective digital data item. Because the data strand 550 can take the form of synthesized single-stranded DNA, it is sometimes called a "single-stranded data element." The data strand 510 represents a respective digital data item. Other data strands will have different sequences of nucleotides and represent different digital data items. Because the data strand 510 can be the target of queries, it is sometimes called a "target strand" or "T."

As shown, the data strand 510 can include a forward primer 511, which is a conserved region used to prepare samples for sequencing.

The data strand can also include an identifier sequence d(T) 512 that uniquely identifies the strand. d(T) maps the strand to its underlying digital data item, whether stored in a digital or DNA database (or both). Although there can be plural copies of the strand 510, the identifier sequence d(T) 512 can differentiate the strand from other strands representing other digital data items.

Although the data strand 510 is single stranded, the resulting DNA database is made partially double stranded using a single-step PCR reaction starting from IP (the "internal primer") 515, which is conserved across elements in the database. As shown, a sequence IP* 521, which is complementary to IP 515 can be used to start the covering process, which covers the identifier sequence d(T) 512 (and forward primer FP 511) with region 535.

The feature nucleotide sequence f(T) 517 can be a DNA representation of the feature sequence described herein and represents a digital feature of the digital data item that can be queried during multiplex similarity search.

A conserved reverse sequencing primer 518 is available to interact with the query during the query reaction run.

The resulting DNA database element 550 can then be used in the multiplex similarity search technologies as described herein. The DNA database element 550 implements DNA data storage in that it indicates an identifier sequence d(T) that identifies an underlying digital data item as well as a feature sequence f(T) that represents a value of one or more features of the underlying digital data item.

The DNA database element 550 can both store and process data. The sequence d(T) 512 stores an identifier unique to the digital data item, and the sequence f(T) 517 is generated from the semantic features of the digital data item, designed as a locus for a hybridization probe. The sequence d(T) 512 is not an active site, but rather the information to be retrieved from the search. For example, it can be the address of a digital data item in another database that stores the digital data item's complete data.

Example 8—Example Feature Sequence

In any of the examples herein, a feature nucleotide sequence f(T) (or simply "feature sequence") can represent a feature value of a digital data item by representing a value for one or more features of the digital item as a nucleotide sequence. In practice, a digital feature value of the digital data item is transformed into a nucleotide sequence as described herein so that the digital feature value is represented in such a way that reverse complementary representations of similar feature values tend to bind to f(T).

Example features of digital data items include data values such as numerical values, media (e.g., images, sounds, video, or the like), or other data types (e.g., sets, vectors, or the like). The digital bits representing a feature value can be encoded into a digital representation of the feature sequence, which is then encoded as a physical sequence of nucleotides (e.g., an oligonucleotide) that represents the feature sequence as a DNA feature sequence.

Example 9—Example System Creating Query Strands

Figure 6:
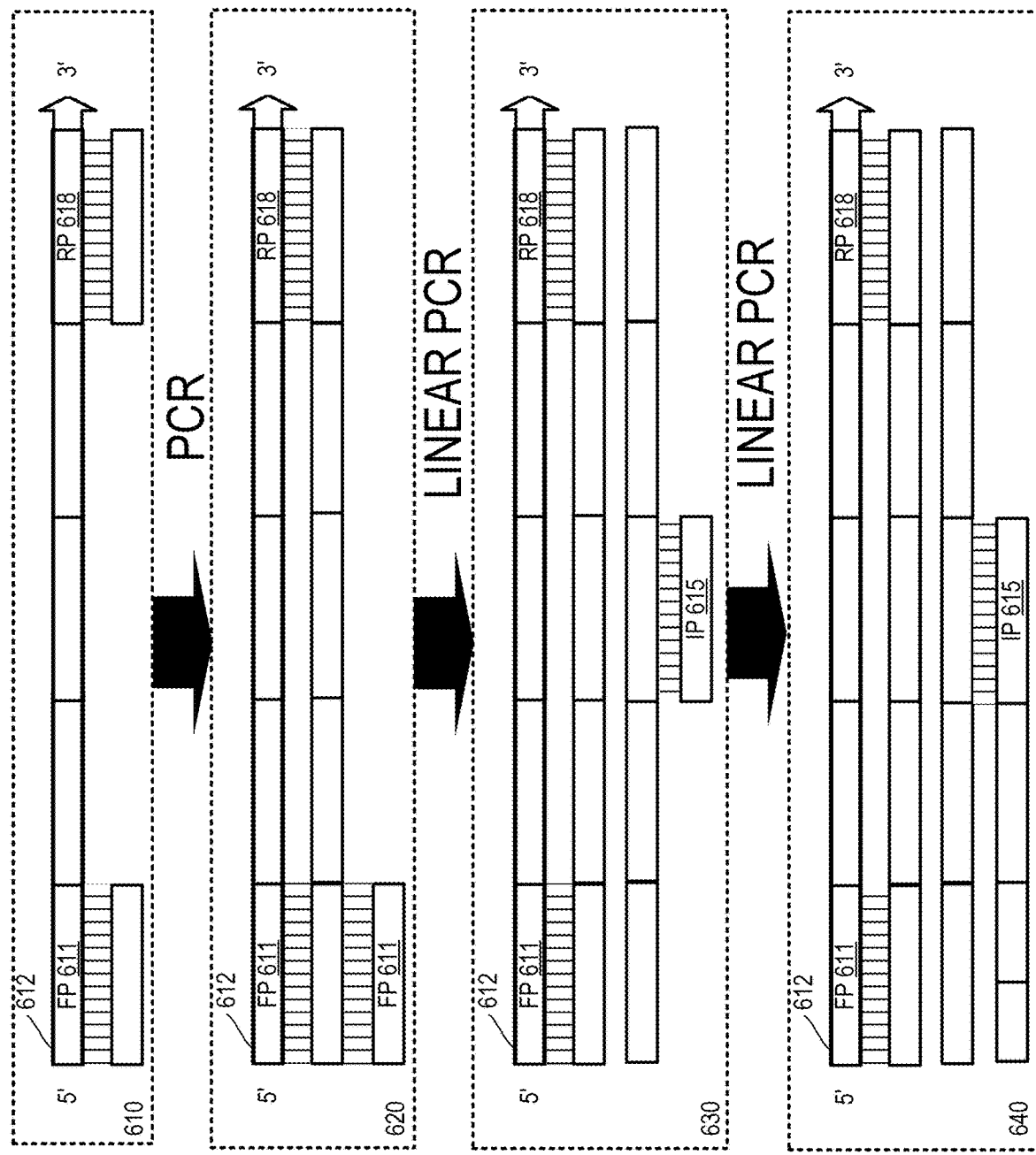
FIG. 6 is a block diagram of an example process of creating DNA database elements for multiplex similarity search in DNA storage.

FIG. 6 is a block diagram of an example process 600 of creating DNA database elements for multiplex similarity search in DNA storage. The original data strand 612 can be any of the data strands described herein and typically include a forward primer 611 and a reverse primer 618 in the arrangement shown in 610.

An exponential PCR technique is then used to amplify the data strand 612, resulting in multiple copies as shown in 620.

Then, a linear PCR technique is used to create single-stranded oligonucleotides using forward primers 611 as shown in 630.

Then, a covering technique is used to cover the identifier sequence as described herein, resulting in the arrangement shown in 640.

Example 10—Example System Creating DNA Query Strands

Figure 7:
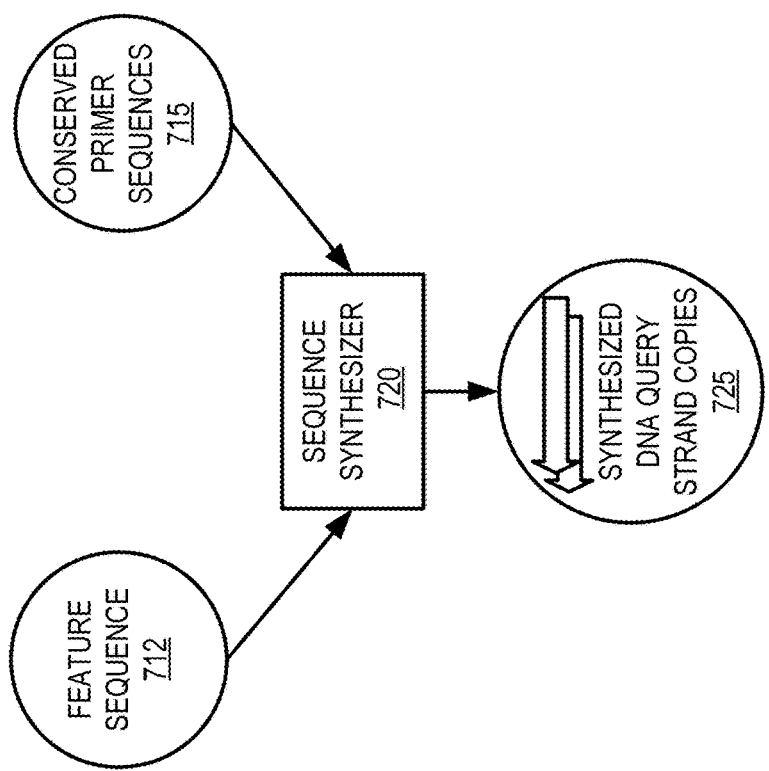
FIG. 7 is a block diagram of an example system creating query strands for multiplex similarity search in DNA data storage.

FIG. 7 is a block diagram of an example system 700 creating DNA query strands for multiplex similarity search in DNA data storage. In the example, a sequence synthesizer 720 accepts a feature sequence 712 and conserved primer sequences 715 as input and outputs synthesized DNA query strand copies 725. In practice, the system is used in parallel with other systems and/or the process is repeated, generating more DNA query strands with different feature sequences 712 to achieve multiplex similarity search.

In the example, over billions of copies of the DNA query strand can be synthesized; therefore, the strand does not need to be amplified.

Example 11—Example Method of Creating DNA Query Strands

Figure 8:
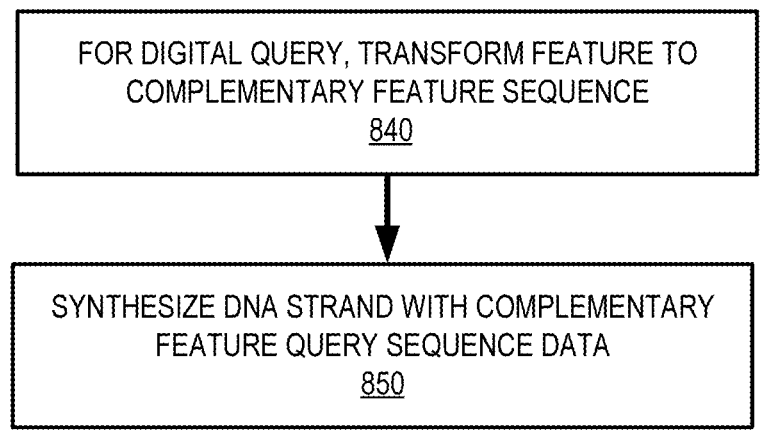
FIG. 8 is a flowchart of an example method of creating query strands for multiplex similarity search in DNA data storage.

FIG. 8 is a flowchart of an example method 800 of creating DNA query strands for multiplex similarity search in DNA data storage that can be used in any of the examples herein and can be performed, for example, by the system of FIG. 7.

At 840, a given digital query is transformed into a (reverse) complementary feature sequence, f(Q)*. In practice, the digital query specifies one or more target feature values for a feature. The digital query is encoded as a complementary feature sequence that queries for data items having feature values for the feature that are similar to the target feature values.

The complementary feature sequence f(Q)* also uniquely identifies the digital query, allowing determination of from which digital query a result strand originated. It thus can be described as an identifier region of the query strand.

Digital feature values of the digital data items can be represented in such a way, and the transformation can be done so that the complementary feature sequence f(Q)* binds to DNA database elements representing digital data items that exhibit feature values that are similar to the feature value of the digital query (e.g., which itself can be a digital representation of a digital feature value) as described herein.

In an embodiment, the transformation can be achieved by using neural network trained to generate appropriate sequences as described herein. The process of generating the complementary feature sequence can thus comprise applying the training data in conjunction with a neural network accepting the digital query (e.g., a feature value).

At 850, a DNA query strand is synthesized with the complementary feature sequence data. The conserved primers P2, RP[:N]*, and RP[-N:] * and region PT can also be included as described herein. Such regions can be incorporated (e.g., identically) across query strands for the different queries so that they can be processed in a uniform way during multiplex operations.

As noted, many copies of the strand can be synthesized (e.g., with the same complementary feature nucleotide sequence). In practice, the resulting DNA query strands can then be used with DNA query strands constructed from other digital feature queries (e.g., with different feature values) in a multiplex reaction as described herein.

Example 12—Example DNA Query Strand

Figure 9:
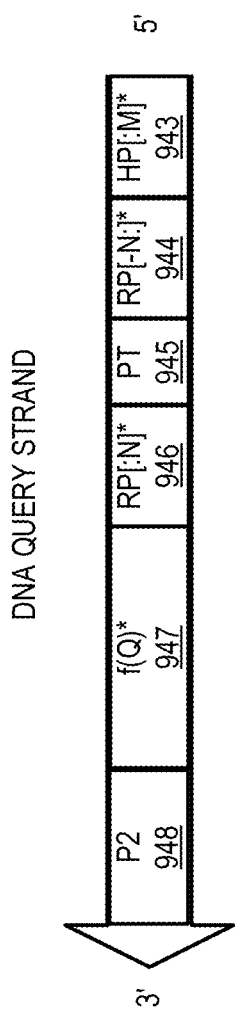
FIG. 9 is a block diagram of an example query strand for multiplex similarity search in DNA data storage.

FIG. 9 is a block diagram of an example DNA query strand 900 for multiplex similarity search in DNA data storage that can be used in any of the examples herein. For sake of simplicity, a DNA query strand is sometimes simply called a "query strand" herein. The query strand 900 can take the physical form of an oligonucleotide.

In the example, the query strand 900 comprises a primer P2 948, the complementary feature sequence f(Q)* 947, primer RP[:N]* 946, a neutral region PT 945 and primer RP[-N:]* 944. RP[:N]* 946 is complementary to the first n bases of the RP region of the DNA data strand (e.g., of FIGS. 5 and 6). RP[-N:]* is complementary to the last n bases of RP. PT 945 is not complementary to RP at all. n can be a number around 5 (e.g., 4, 5, 6, or the like). The short 5-base complementary sequences allow the ends to be stable and to be ligated to the linking strand as described herein, but they are also not too stable to cause the query strand to bind if f(Q)* does not bind strongly to F(T). The ligation assisting combination RP[:N]* 946, PT 945, RP[-N-]* 944 serves to assist in ligation as described herein.

The query strand 900 can also comprise a partial complementary linking strand primer region comprising primer HP[:M]* 943. HP[:M]* 943 is complementary to the first m bases of the HP region of the linking strand or linking strand element (e.g., of FIG. 13 et al.). As described elsewhere herein, another region HP [-M:]* can be used to achieve binding. m can be a number around 5 (e.g., 4, 5, 6, or the like). The short 5-base complementary sequence facilitates ligation and binding to a linking strand or linking element as described herein.

The complementary feature sequence f(Q)* 947 can serve as an identifier of the query strand and thus an identifier of the underlying digital query, facilitating multiplex query operation by allowing determination of the digital query that generated a particular result strand among result strands generated by one or more other digital feature queries.

Example 13—Example System Matching Query to Data

Figure 10:
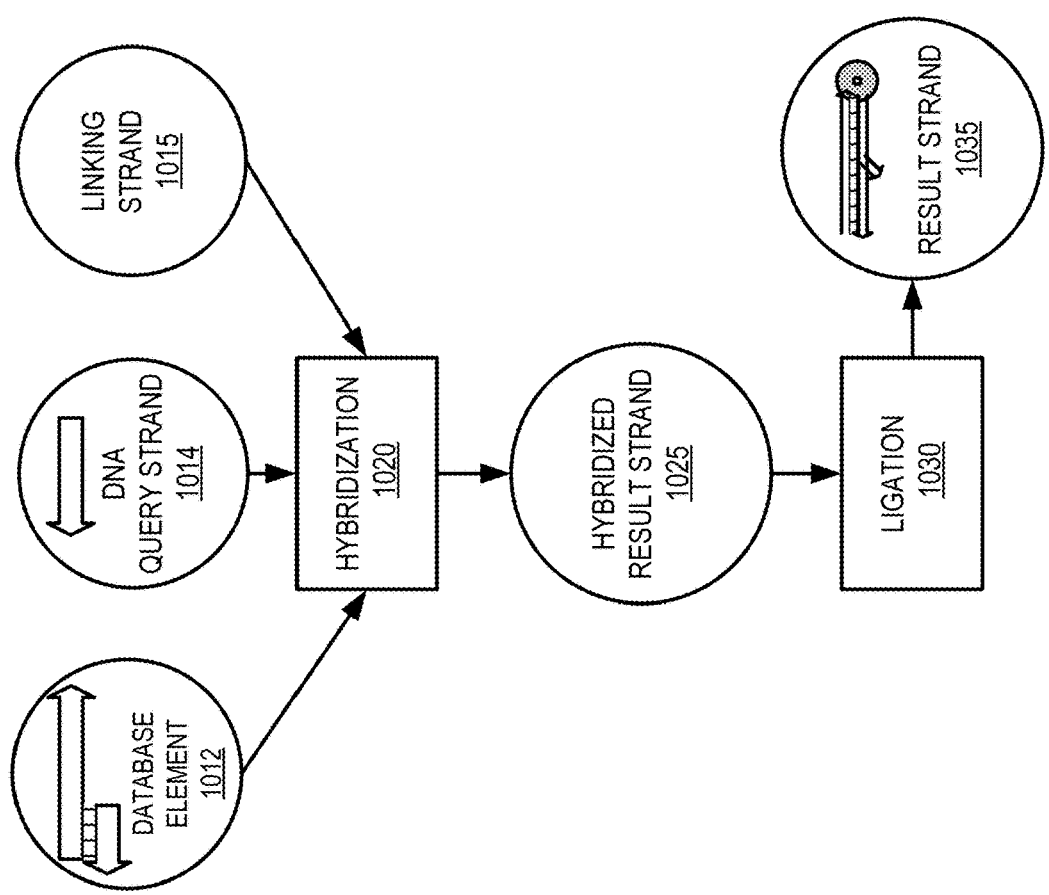
FIG. 10 is a block diagram of an example system matching query elements to DNA database elements in a query reaction run for multiplex similarity search in DNA data storage.

FIG. 10 is a block diagram of an example system 1000 matching query elements to DNA database elements in a query reaction run for multiplex similarity search in DNA data storage. In the example, a single query reaction run (e.g., hybridization 1020) can result in not just the single result strand as shown, but multiple result strands, and the result strands can be for different query strands representing different digital feature queries.

The hybridization process 1020 can involve a DNA database element 1012, a query strand 1014, and the linking strand 1015 and produce a hybridized result strand 1025. A ligation reaction 1030 can be used so that the linking strand fully links to the DNA query strand 1014 and to the DNA data strand (e.g., of the DNA database element 1014 that matches the DNA query strand 1014).

The result strand 1035 can then be further processed and indicates both the matching digital data item and the associated digital query in a single structure. Sequencing can reveal the results of the query run. In practice, there are multiple result strands 1035 in the multiple reaction of a single query run.

Example 14—Example Method of Matching Query to Data

Figure 11:
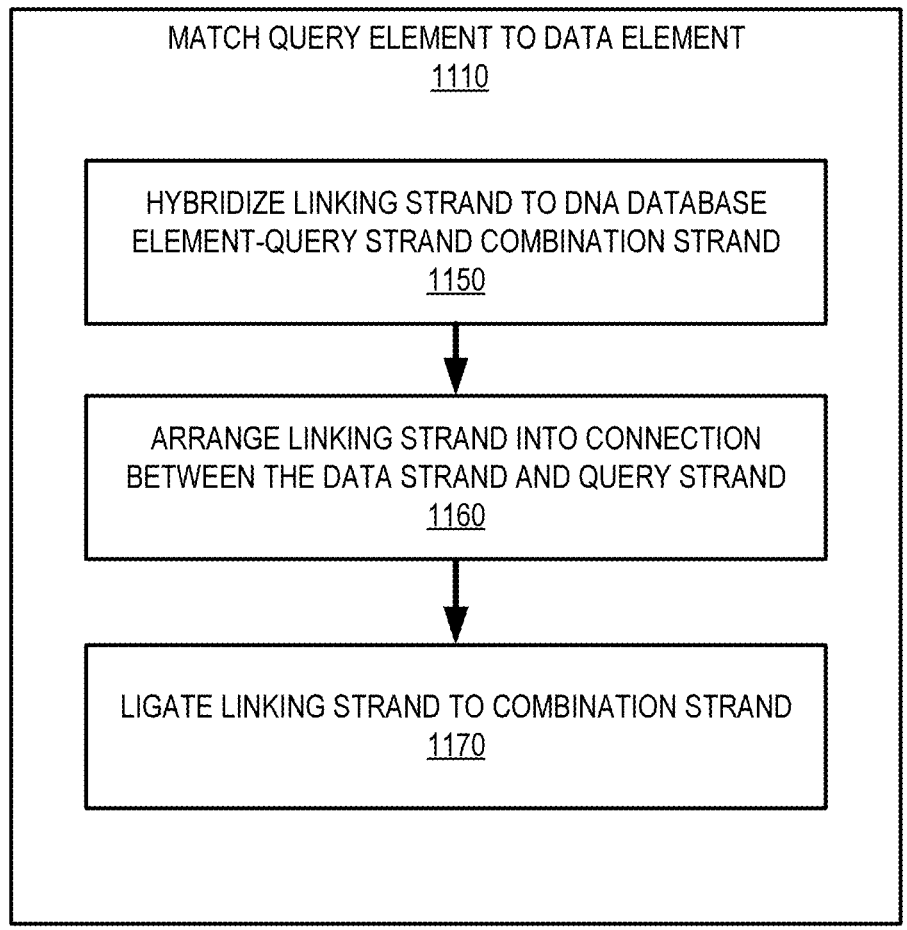
FIG. 11 is a flowchart of an example method of matching query elements to DNA database elements in a query reaction run for multiplex similarity search in DNA data storage.

FIG. 11 is a flowchart of an example method 1100 of matching query elements to DNA database elements in a single query reaction run for multiplex similarity search in DNA data storage that can be used in any of the examples herein and can be performed, for example, by the system of FIG. 10. In the example, ligation is used in combination with a DNA linking strand to link a DNA data strand of a DNA database element and a query strand. As with other methods described herein, the order of the actions can be changed according to use case.

At 1150, a DNA linking strand is hybridized to a DNA database element-DNA query strand combination strand (e.g., the database element that matches the DNA query strand).

At 1160, the linking strand is arranged into a connection between the DNA data strand of the DNA database element and the DNA query strand.

At 1170, the linking strand is ligated to the combination strand so that the DNA database element is linked to the DNA query strand for later sequencing to determine the query results.

As described herein, various embodiments can be used to achieve the method 1110. Two examples are called "linking-strand-early" and "linking-strand-late" techniques herein.

Example 15—Example Result Strand with Linking Strand

Figure 12:
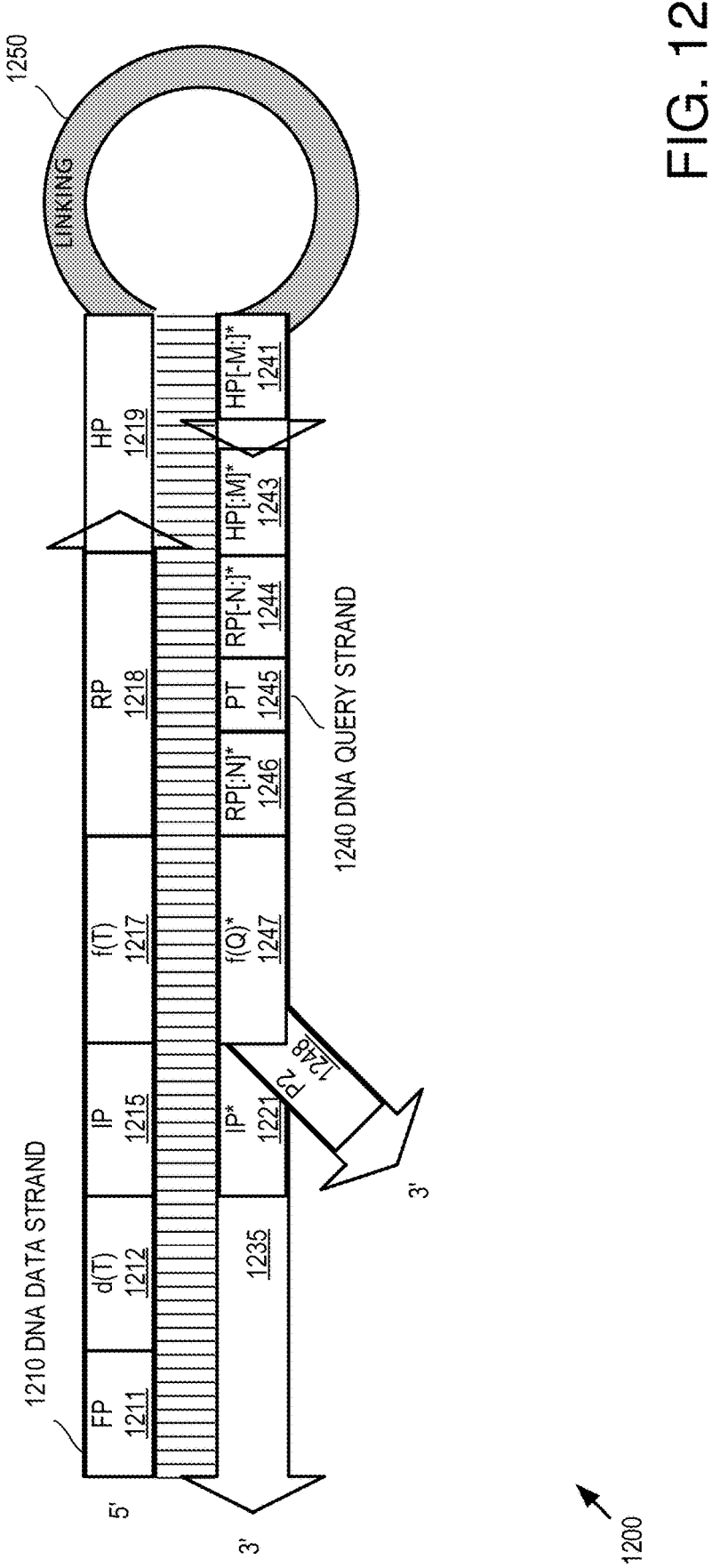
FIG. 12 is a block diagram of an example result strand for multiplex similarity search in DNA data storage.

FIG. 12 is a block diagram of an example result strand 1200 with linking strand for multiplex similarity search in DNA data storage that can be used in any of the examples herein. The DNA structure 1200 is formed and present after the query run (hybridization) and ligation are performed as described herein.

The result strand 1200 comprises the DNA data strand 1210 and the DNA query strand 1240 that matches the DNA data strand 1210. The data strand comprises the regions FP 1211, d(T) 1212, IP 1215, f(T) 1217, and RP 1218 as described herein.

The DNA query strand 1240 comprises the regions P2 1248, f(Q)* 1247, RP[:N]* 1246, PT 1245, and RP[–N:]* 1244, (e.g., as described in FIG. 9).

Additional regions HP 1219, HP[:M]* 1243, and HP[–M:]* 1241 (e.g., as described in FIG. 9), and the linking strand 1250 can also be included as described herein to achieve a connection between the DNA data strand 1210 and the DNA query strand 1240 that facilitates multiplex similarity search.

The result strand 1200 also includes regions IP* 1221 and covering region 1235 that are part of the respective DNA database element associated with the DNA data strand 1210.

Similarity search can be achieved because f(T) 1217 need not be completely complementary to f(Q)*. Instead, sufficient similarity between the two will result in binding, thus achieving similarity search as described herein.

Example 16—Example Matching

In any of the examples herein, the term "match" need not require a complete or identical match. As described herein, matching can be achieved through hybridization, which does not require a strict one-to-one reverse complementarity between the nucleotides of f(T) and f(Q)*. Thus, matching can achieve similarity search as described herein in that data strands having features similar to features represented in query strands can hybridize to the query strands and thus match.

Example 17—Example Linking-Strand-Late Technique

Figure 13:
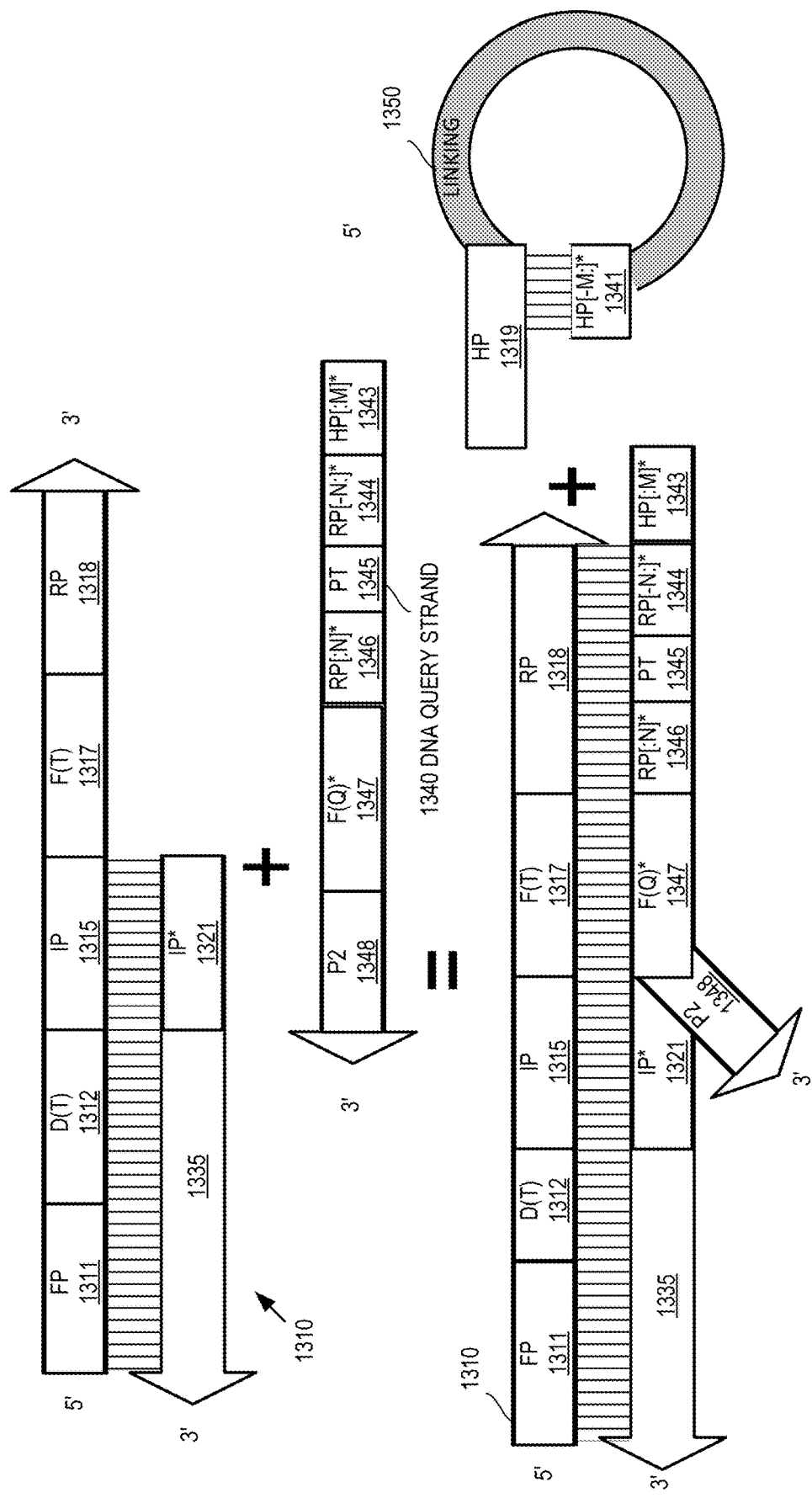
FIG. 13 is a block diagram of an example linking-strand-late technique that binds a linking strand to a preliminary result strand for multiplex similarity search in DNA data storage.

FIG. 13 is a block diagram of an example linking-strand-late technique that binds a linking strand element 1350 to a preliminary result strand for multiplex similarity search in DNA data storage that can be used in any of the examples herein.

In the example, a DNA database element 1310 comprises regions FP 1311, d(T) 1312, IP 1315, f(T) 1317, RP 1318, IP* 1321 and covering region 1335 as described herein. The DNA query strand 1340 comprises regions P2 1348, f(Q)* 1347, RP[:N]* 1346, PT 1345, RP[–N:]* 1344, and HP[:M]* 1343 as described herein (e.g., with respect to FIG. 9).

A linking strand element 1350 comprises a region HP 1319 and HP [–M:]* 1341.

After the two strands 1310 and 1340 are hybridized together into a preliminary result strand, the linking strand element 1350 with attached region HP 1319 and HP [–M:]* 1341 is hybridized to region HP[:M]* 1343 to place the linking strand 1350 at an appropriate location. The resulting DNA structure is shown in FIG. 14.

Example 18—Example Ligation for Linking-Strand-Late Technique

Figure 14:
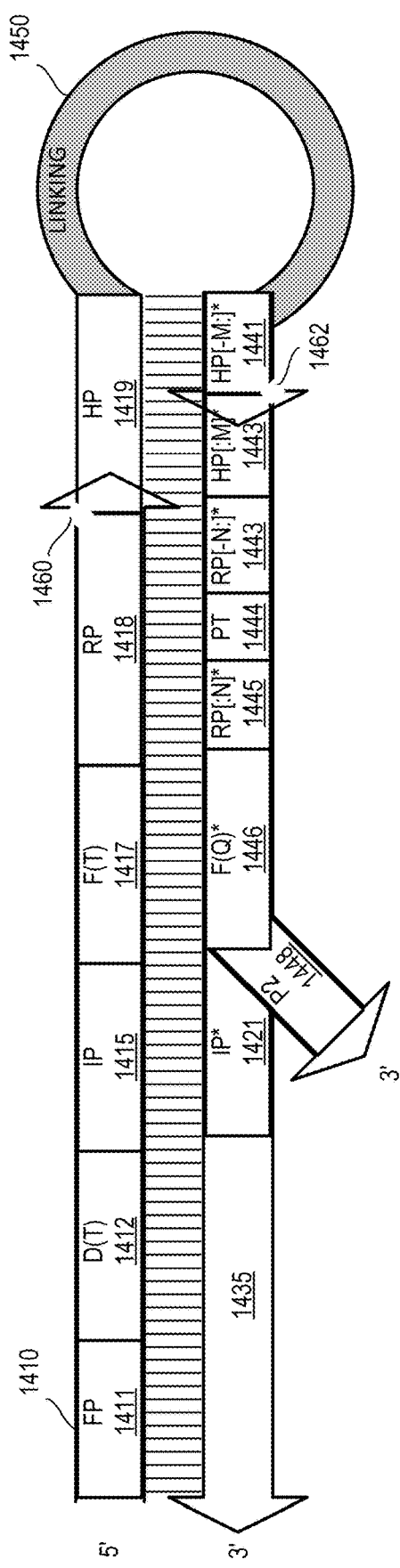
FIG. 14 is a block diagram of an example ligation technique for a linking-strand-late technique that binds a linking strand to a preliminary result strand for multiplex similarity search in DNA data storage.

FIG. 14 is a block diagram of an example ligation technique for a linking-strand-late technique that binds a linking strand to a preliminary result strand 1400 for multiplex similarity search in DNA data storage. Although the linking strand 1450 is in an appropriate position to connect the data strand to the query strand, there are still nicks at 1460 and 1462. A ligation process can be applied to fill the nicks (e.g., completing the connection between the data strand of the data element and the query strand), resulting in the complete result strand (e.g., as shown in FIG. 12).

The remaining regions 1410-1448 can be as described herein (e.g., in FIGS. 5, 9, et al.).

Example 19—Example Linking-Strand-Late Method of Generating a Result Strand

FIG. 15 is a flowchart of an example linking-strand-late method 1500 of generating a result strand for multiplex similarity search in DNA data storage and can be performed, for example, to implement the technologies of FIG. 13 and FIG. 14.

At 1540, the query element is hybridized to the DNA database element.

At 1550, the linking element is hybridized to the preliminary result strand (e.g., the DNA database element—query strand combination strand).

At 1560, the nicks (e.g., two nicks) described herein in the linking-strand-late technique are filled via ligation.

Example 20—Example Linking-Strand-Early Technique: Query Strand

Figure 16:
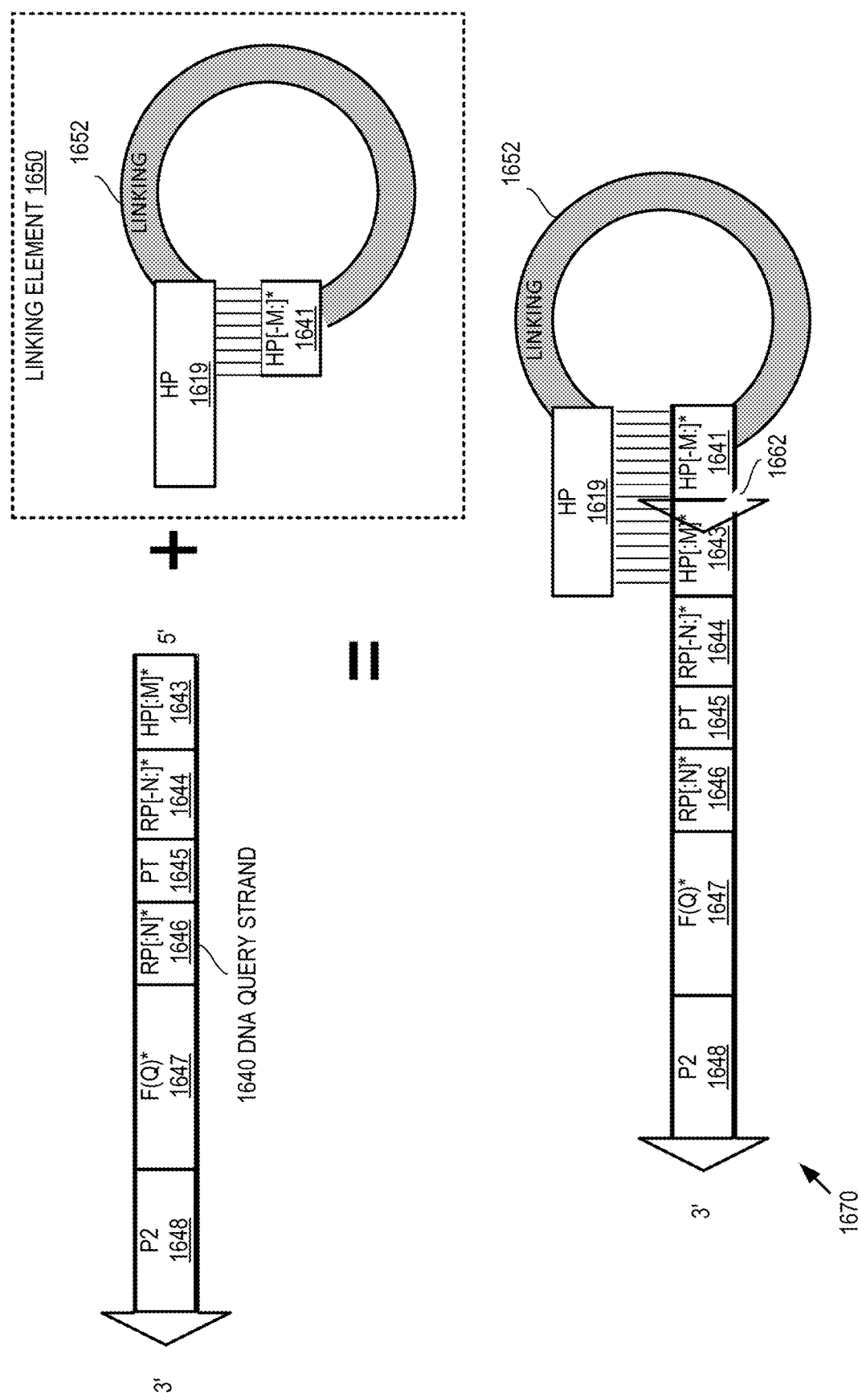
FIG. 16 is a block diagram of an example linking-strand-early technique that binds a linking strand to a query strand for multiplex similarity search in DNA data storage and includes ligation.

FIG. 16 is a block diagram of an example linking-strand-early technique that binds a linking strand to a query strand for multiplex similarity search in DNA data storage and includes ligation; it can be used in any of the examples herein.

In the example, a DNA query strand 1640 comprises regions P2 1648, f(Q)* 1647, RP[:N]* 1646, PT 1645, RP[–N:]* 1644, and HP[:M]* 1643 as described herein (e.g., in FIG. 9 et al.). The DNA linking element 1650 comprises a linking strand 1652, a region HP [–M:]* 1641, and a region HP 1619 that is used to bind the DNA linking element 1650 to the DNA query strand 1640. As a result, a DNA query strand—DNA linking strand element combination element 1670 is created, and it contains a nick 1662, which can be ligated (e.g., either before or after the hybridization reaction of the query reaction run is performed). The resulting query-linking element can be used during the query reaction run as shown in FIG. 17.

Example 21—Example Linking-Strand-Early Technique: Result Strand

Figure 17:
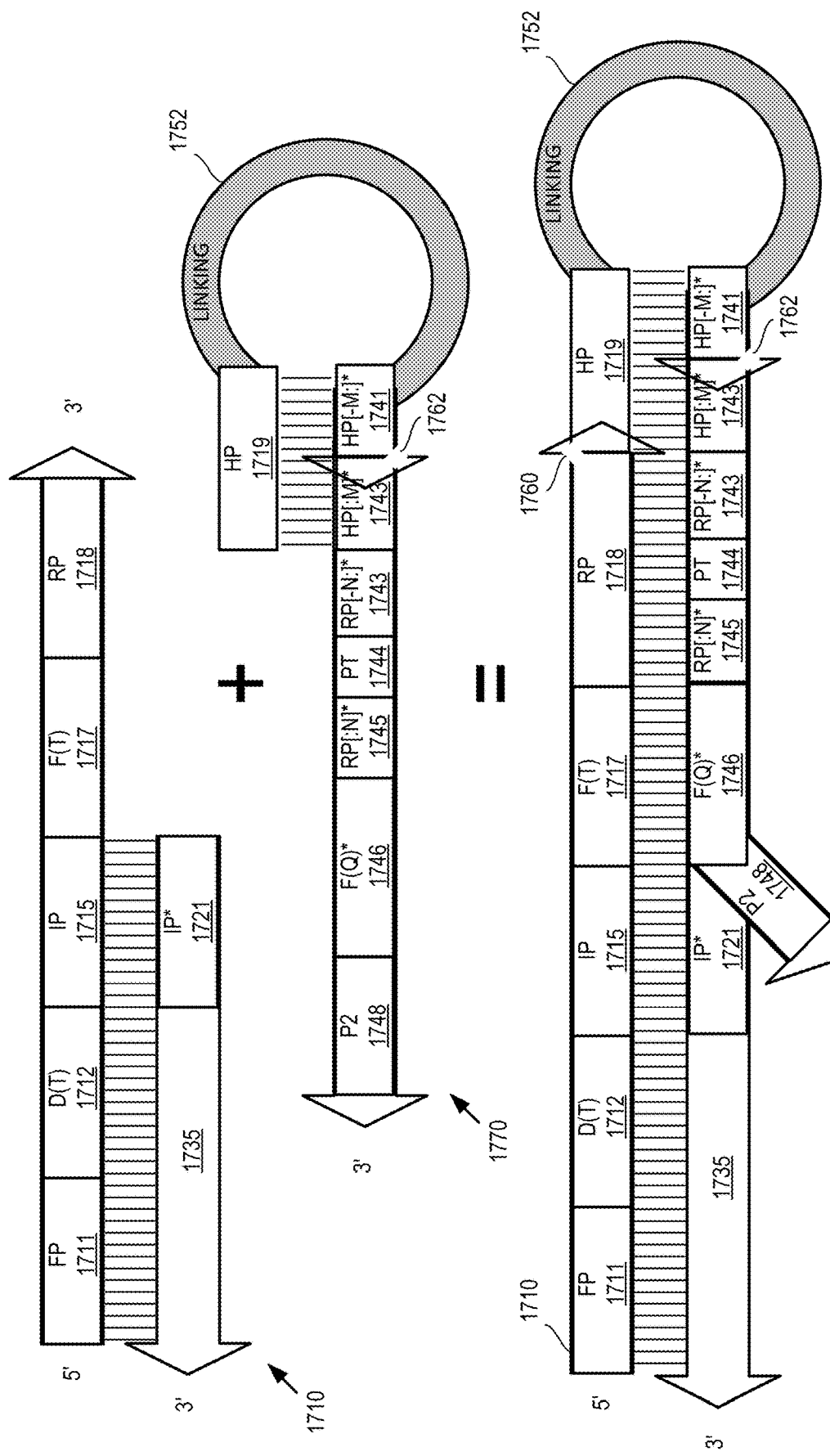
FIG. 17 is a block diagram of an example linking-strand-early technique that binds a data strand to a query-linking strand for multiplex similarity search in DNA data storage.

FIG. 17 is a block diagram of an example linking-strand—early technique that binds a DNA database element 1710 to a query-linking element 1770 for multiplex similarity search in DNA data storage.

In the example, the DNA database element 1710 is hybridized to the query-linking element (e.g., of FIG. 16), resulting in a preliminary result strand 1780, which includes a nick 1760 that is ligated to connect the DNA data strand of the DNA database element 1710 to the query element of the element 1770. Although nick 1762 is shown in the example, it can alternatively be ligated beforehand.

The regions 1711-1748 can be as elsewhere described herein.

Processing can then be performed on the complete result strand to determine query results.

Example 22—Example Linking-Strand-Early Method of Generating a Result Strand

Figure 18:
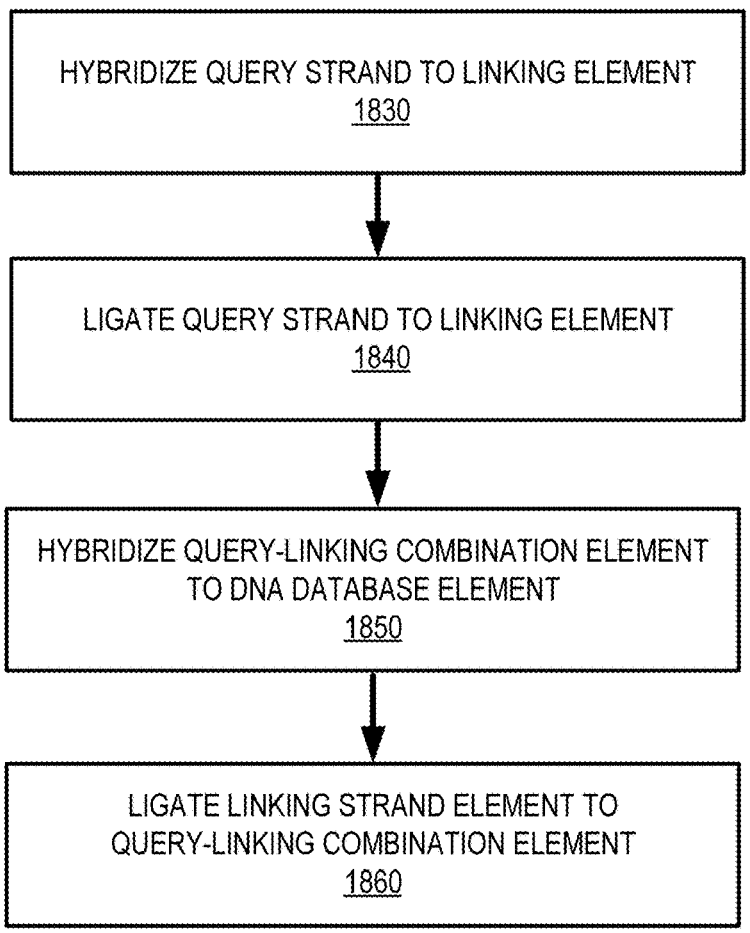
FIG. 18 is a flowchart of an example linking-strand-early method of generating a result strand for multiplex similarity search in DNA data storage.

FIG. 18 is a flowchart of an example linking-strand-early method 1800 of generating a result strand for multiplex similarity search in DNA data storage and can be performed, for example, to implement the technologies of FIG. 16 and FIG. 17.

At 1830, the DNA query strand is hybridized to the DNA linking element.

At 1840, a ligation technique is used to fill the nick between the query strand and the linking element. This can be done before or after hybridization.

At 1850, the query-linking element is hybridized to its matching DNA database element.

At 1860, a ligation technique is used to fill the remaining nick (e.g., between the linking strand element and the data strand). The nicks can be filled in either order.

Example 23—Example Linking Strand

In any of the examples herein, a DNA linking strand can be used to connect a query strand to its matching data strand, which enables multiplex similarity search. As described herein, the linking strand can be incorporated into a larger linking element that facilitates positioning the linking strand into a position that connects the query strand to the data strand, and the connection can be completed via a ligation process.

In one implementation, the linking strand can take the form of a DNA hairpin. In practice, the hairpin can be 4-10 (e.g., 4, 5, 6, 7, 8, 9, or 10) nucleotides in length. The sequences in the hairpin domain can be chosen so they have no self-interaction. For example, polyT (e.g., TTTTT) can be used. As described herein, the hairpin can be part of a linking element (e.g., hairpin element) that has other sequences that assist in linking the data strand to the query strand, ultimately resulting in a connection after ligation.

The hairpin can be made longer or shorter, but such is typically not necessary.

The hairpin element can take the form of a loop in a fold, causing several bases to remain unpaired before the hairpin element (e.g., strand) loops back on itself (e.g., as shown in the drawings herein).

Example 24—Example Multiplex Similarity Search Query Reaction Run (Hybridization)

In any of the examples herein, a query reaction run can involve assembling a physical quantity of data elements (e.g., plural instant copies of particular data elements for a data strand, where there are plural digital data elements represented by the data strands) and a physical quantity of query strands (e.g., plural instant copies of particular query strands representing different digital queries) and then creating conditions in which hybridization between the two will occur (e.g., mixing them together and observing a protocol similar to that described in Example 49, but in a multiplex context).

There are different ways to get to the unwound strand (e.g., FP-d(T)-IP-f(T) . . . -f(Q)-P2 as shown in FIG. 20. For example, size selection using a denaturing gel can be applied, which selects the fully ligated unwound strand. Another technique is to perform a PCR using the primer pair of FP and P2. The primer pair will selectively amplify only the ligated unwound strand. In practice, there will be plural unwound strands for sequencing.

Example 25—Example Amplification of Result Strands

In any of the examples herein, result strands can be amplified (e.g., via PCR as described in Example 49 to increase the strands available for sequencing. The ligated strand is a single-stranded structure. If both a forward and reserve primer are used, it can be amplified to become double-stranded and amplified exponentially. If only a reserve primer is used, the single strand can be amplified linearly.

Example 26—Example Method of Processing Result Strand

Figure 19:
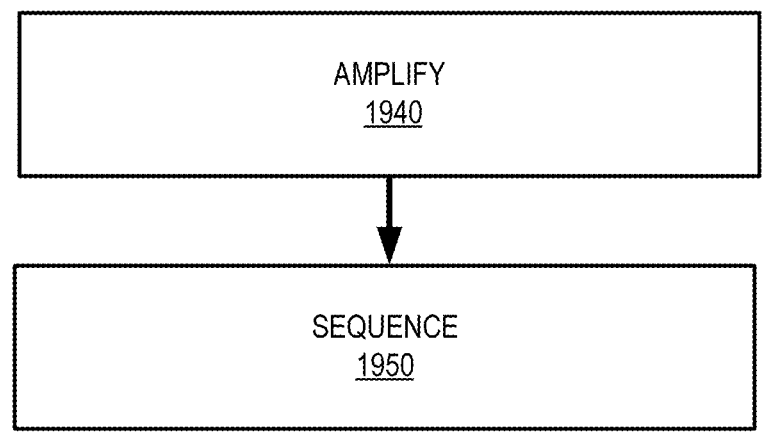
FIG. 19 is a flowchart of an example method of processing a result strand for multiplex similarity search in DNA data storage.

FIG. 19 is a flowchart of an example method 1900 of processing a result strand for multiplex similarity search in DNA data storage and can be performed, for example, on the result strands of a query reaction run in any of the examples herein. As described herein, the result strand can be denatured. However, typically, sequencers can take double-stranded oligos as input and denaturing can be performed in the sequencer device.

At 1940, the result strand is amplified. In any of the examples herein, the result strands of a query reaction run can be amplified as described herein (along with other result strands in the multiplex similarity search), resulting in a large number of result strands to facilitate accurate sequencing.

The ligated strand can be exponentially amplified, while the covering strand (e.g., 1735 and IP* 1721) is not. Therefore, regardless if the covering strand still attaches to the result strand or not, the population of the covering strand becomes so small and insignificant compared to the amplified oligos (e.g., the ligated full-length oligo that contains the data strand and the query strand).

At 1950, the amplified result strands are sequenced. The result is a digital representation of the regions of the result strand (e.g., so called "raw results"). Further processing can be performed to determine actual query results.

Example 27—Example Sequencing

The result strands may be sequenced with a polynucleotide sequencer. In some implementations, DNA strands may be prepared for sequencing by amplification using polymerize chain reaction (PCR) to create a large number of DNA strands that are identical copies of each other. The need for PCR amplification prior to sequencing may depend on the specific sequencing technology used. PCR may itself be a source of error, although at a much lower level than current sequencing technology. At present, PCR techniques typically introduce one error per 10,000 bases. Thus, on average, for every 100 reads of 100 bases there will be one error that is the result of PCR. The errors introduced by PCR are generally distributed randomly so the trace reconstruction system will be able to correct some PCR-induced errors.

The polynucleotide sequencer reads the order of nucleotide bases in a DNA strand and generates one or more reads from that strand. Polynucleotide sequencers use a variety of techniques to interpret molecular information and may introduce errors into the data in both systematic and random ways. Errors can usually be categorized as substitution errors, where the real code is substituted with an incorrect code (for example A swapping with G), insertions, or deletions, where a random unit is inserted (for example AGT becoming AGCT) or deleted (for example AGTA becoming ATA). Each position in a read is an individual base call determined by the polynucleotide sequencer based on properties sensed by components of the polynucleotide sequencer. The various properties sensed by the polynucleotide sequencer vary depending on the specific sequencing technology used. A base call represents a determination of which of the four nucleotide bases—A, G, C, and T (or U)—in a strand of DNA (or RNA) is present at a given position in the strand. Sometimes the base calls are wrong and this is a source of error introduced by sequencing. Polynucleotide sequencing includes any method or technology that is used to generate base calls from a strand of DNA or RNA.

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technique that can be used is nanopore sequencing. A nanopore is a small hole of the order of 1 nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technology that can be used includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure that enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another sequencing technique that can be used is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into an instrument, e.g., a HeliScope™ sequencer, and a laser illuminates the surface of the flow cell, revealing the position of each template. A CCD camera can map the position of the templates on the flow cell surface. The template fluorescent-label is then cleaved and washed away. The sequencing reaction begins by introducing a DNA polymerase and a fluorescently-labeled nucleotide. The oligo-T nucleic acid serves as a primer. The polymerase incorporates the labeled nucleotides to the primer in a template-directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently-labeled nucleotides until the desired read length is achieved. Sequence information is collected with each nucleotide addition step.

Another example of a DNA sequencing technique that can be used is SOLiD™ technology (Applied Biosystems). In SOLiD™ sequencing, DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, templates, and PCR components. Following PCR, the templates are denatured and beads are enriched to separate the beads with extended templates. Templates on the selected beads are subjected to a 3' modification that permits bonding to a glass slide.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

Technologies for sequencing DNA are associated with some level of error and the type and frequency of errors differs by sequencing technology. For example, sequencing-by-synthesis creates an error in about 2% of the base calls. A majority of these errors are substitution errors. Nanopore sequencing has a much higher error rate of about 15 to 40% and most of the errors caused by this sequencing technology are deletions. The error profile of a specific sequencing technology may describe the overall frequency of errors as well as the relative frequency of various types of errors.

In some implementations, the polynucleotide sequencer provides quality information that indicates a level of confidence in the accuracy of a given base call. The quality information may indicate that there is a high level or a low level of confidence in a particular base call. For example, the quality information may be represented as a percentage, such as 80% confidence, in the accuracy of a base call. Additionally, quality information may be represented as a level of confidence that each of the four bases is the correct base call for a given position in a DNA strand. For example, quality information may indicate that there is 80% confidence the base call is a T, 18% confidence the base call is an A, 1% confidence the base call is a G, and 1% confidence the base call is a C. Thus, the result of this base call would be T because there is higher confidence in that nucleotide being the correct base call than in any of the other nucleotides. Quality information does not identify the source of an error, but merely suggests which base calls are more or less likely to be accurate.

The polynucleotide sequencer provides output, multiple noisy reads (possibly of multiple DNA strands), in electronic format to a trace reconstruction system. The output may include the quality information as metadata for otherwise associated with the reads produced by the polynucleotide sequencer.

The trace reconstruction system can be implemented as an integral part of the polynucleotide sequencer. The polynucleotide sequencer can include an onboard computer that implements the trace reconstruction system. Alternatively, the trace reconstruction system may be implemented as part of a separate computing device that is connected to the polynucleotide sequencer through a wired or wireless connection. For example, the computing device may be a desktop or notebook computer used to receive data from and/or to control the polynucleotide sequencer. A wired connection may include one or more wires or cables physically connecting the computing device to the polynucleotide sequencer. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. The trace reconstruction system may also be implemented as part of a cloud-based or network system using one or more servers that communicate with the polynucleotide sequencer via a network. The network may be implemented as any type of communications network such as a local area network, a wide area network, a mesh network, an ad hoc network, a peer-to-peer network, the Internet, a cable network, a telephone network, and the like.

Additionally, the trace reconstruction system may be implemented in part by any combination of the polynucleotide sequencer, the computing device, and the servers.

The trace reconstruction system outputs a digital representation of the result strands for further processing as described herein.

Example 28—Example Unwound Result Strand

FIG. 20 is a block diagram of an example unwound result stand 2000 for multiplex similarity search in DNA data storage. Due to the ligation reactions described herein, the unwound result strand 2000 comprises both the query strand and its matching data strand. In practice, the result strands of a query reaction run can be amplified (along with other result strands in the multiplex similarity search), resulting in a large number of unwound result strands 2000 to facilitate accurate sequencing.

The most relevant portions of the unwound result strand 2000 are the identifier sequence d(T) 2012, which identifies the digital data item that matches the query, and f(Q)* 2046, which identifies the query.

The remaining regions 2011, 2015, 2017, 2018, 2019, 2051, 2042, 2043, 2044, 2045, and 2048 can be as described herein.

Example 29—Example System Processing Query Results

Figure 21:
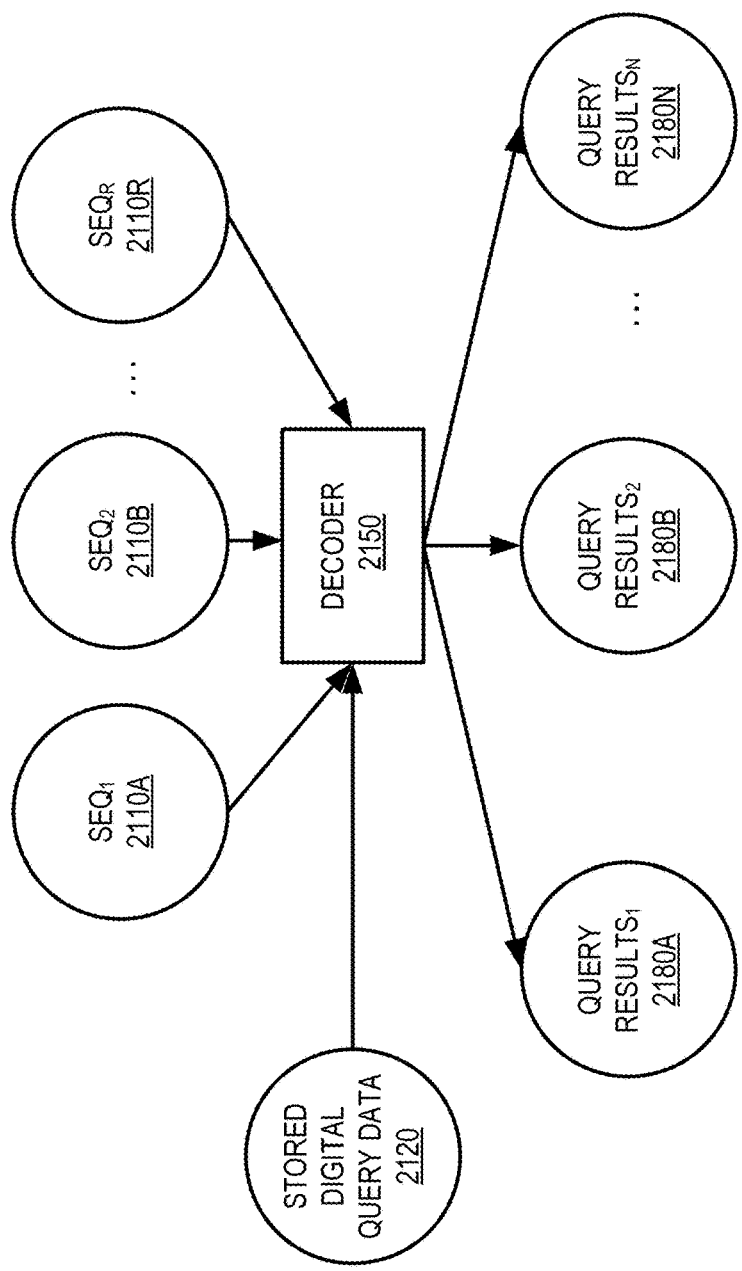
FIG. 21 is a block diagram of an example system processing query results for multiplex similarity search in DNA data storage.

FIG. 21 is a block diagram of an example system 2100 processing query results for multiplex similarity search in DNA data storage. In the example, a sequencer outputs a plurality of digital sequences $SEQ_{1-r}$ 2110A-R that have been read from result strands produced from a multiplex similarity search query reaction run (so-called "raw results"). In practice, the digital sequences 2110A-R can be filtered based on length and/or confidence score before processing and are used as input digital sequences to the decoder 2150. The input digital sequences represent discrete results and can be a digital representation of the unwound result strand depicted in FIG. 20.

The decoder 2150 can decode the raw results of the input sequences 2110A-R. The decoder matches the digital sequences 2110A-R to their respective queries based on the stored digital query data 2120, which maps queries (e.g., a query identifier) to respective complementary feature sequences f(Q)* (and/or can determine the one or more feature values of the query from a mapping). A plurality of sequences from 2110A-R can match a single query because a query can have more than one similarity search result. The decoder can also determine the identity of the digital data items.

The query results 2180A-N indicate, by query, the digital data items that were found to be matching respective of the queries during the query reaction run based on d(T).

Example 30—Example Method of Processing Query Results

Figure 22:
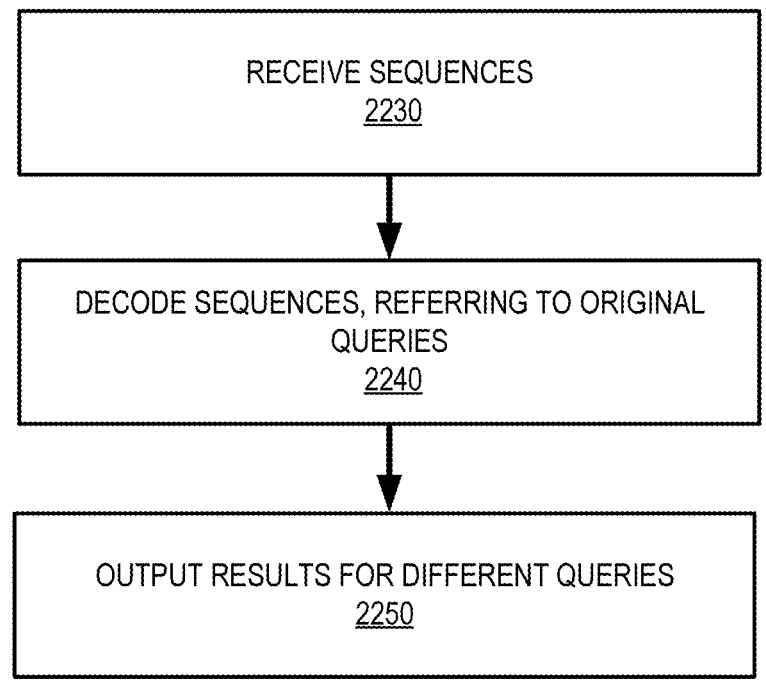
FIG. 22 is a flowchart of an example method of processing query results for multiplex similarity search in DNA data storage.

FIG. 22 is a flowchart of an example method 2200 of processing query results for multiplex similarity search in DNA data storage and can be performed, for example, by the system of FIG. 21.

At 2230, a plurality of input sequences can be received.

At 2240, the sequences can be decoded. Such decoding comprises determining the originating query (e.g., based on mappings to f(Q)*) and an identity of the matching data item (e.g., based on d(T)) for a given sequence (e.g., by virtue of the fact that f(Q)* and d(T) appear on the same sequence).

At 2250, results for the different queries are output. In a multiplex scenario, results for plural, different queries (e.g., queries with different f(Q)*) are output.

Example 31—Example Results: Matching Digital Data Items

Figure 23:
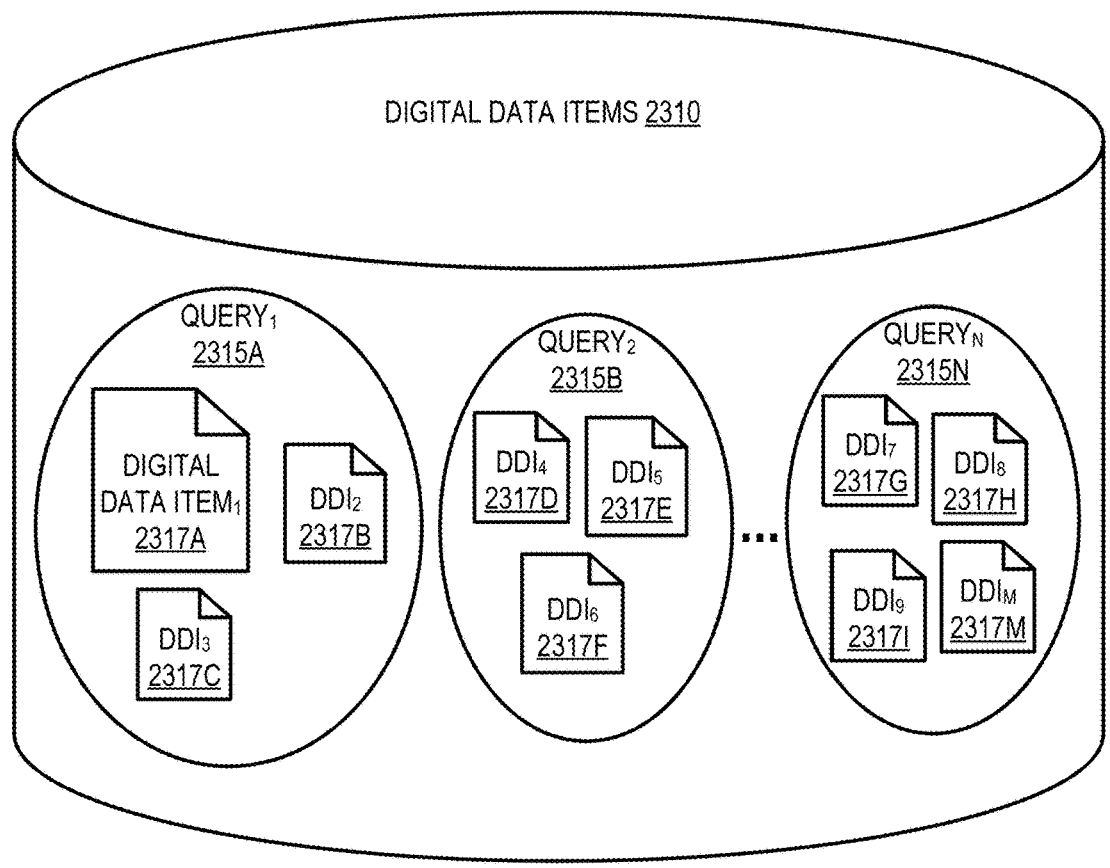
FIG. 23 is a block diagram of example query results described as matching data items.

FIG. 23 is a block diagram of an example query results 2310 described as matching digital data items. The usefulness of the technologies can be enhanced by indicating which digital data items match a particular digital query.

In the example, the matching data items 2310 are indicated as matching a particular query 2315A-N, and the set of matching data items (e.g., 2317A, B, C) for a particular query are stored. Other items 2317D-M can match other queries 2315B-N.

Results can be processed according to the use case(s) for which the queries were performed.

Example 32—Example Advantages

The technologies herein can result in various advantages depending on implementation and context. For example, the ability to perform more than one query per reaction run can result in conservation of resources (e.g., physical resources such as reaction reagents and the like, energy resources to execute the reaction, and the like) and time (e.g., greater throughput in the form of more queries per unit of time).

Separately, due to the linking strand connection, the resulting strands of the query run are of longer length than other strands in the reaction. Therefore, a filtering (e.g., gel) technique can be used to remove shorter strands. Accordingly, the overall accuracy of the result can be improved, even for single-plex reaction runs.

Example 33—Example Digital Perspective

Figure 24:
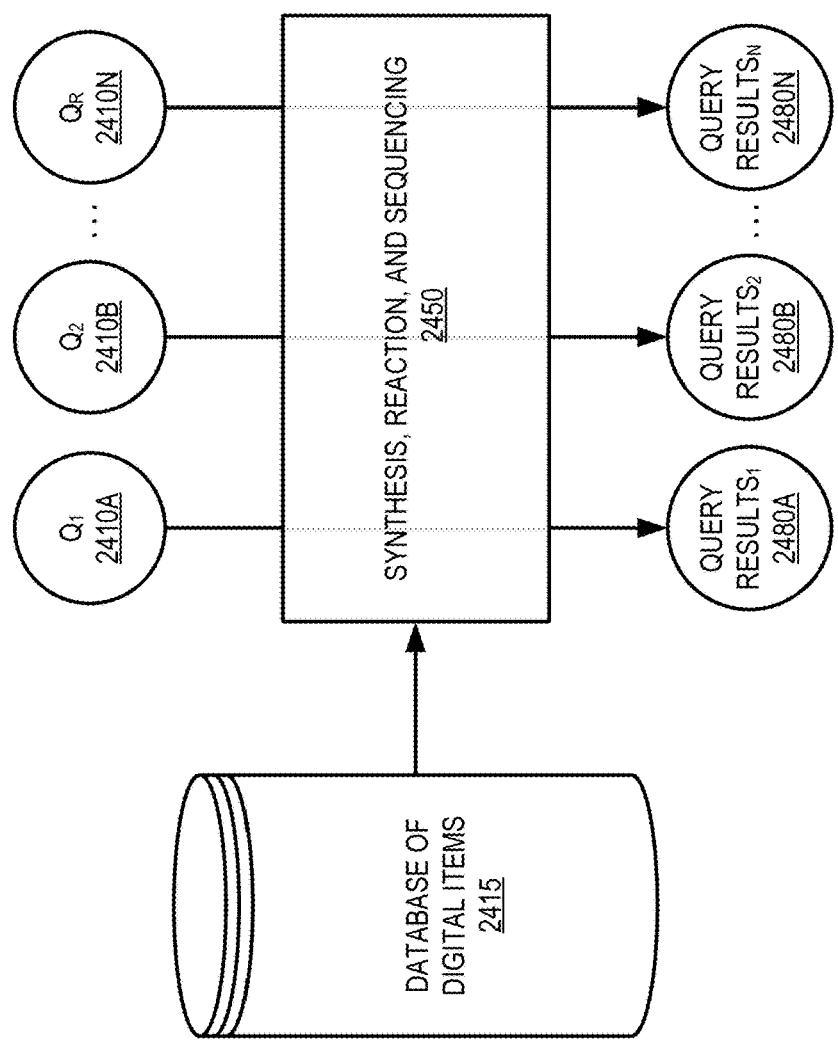
FIG. 24 is a block diagram of an example system implementing multiplex similarity search in DNA data storage from a digital perspective.

The technologies herein can be described from a digital perspective. FIG. 24 is a block diagram of an example system 2400 implementing multiplex similarity search in DNA data storage from a digital perspective.

In the example, a plurality of queries 2410A-N are run against a database of digital items 2415. Synthesis, reaction, and sequencing 2450 are performed as described herein to match DNA representations of digital items to DNA representations queries.

The results can be decoded as query results 2480A-N of the respective queries.

Figure 25:
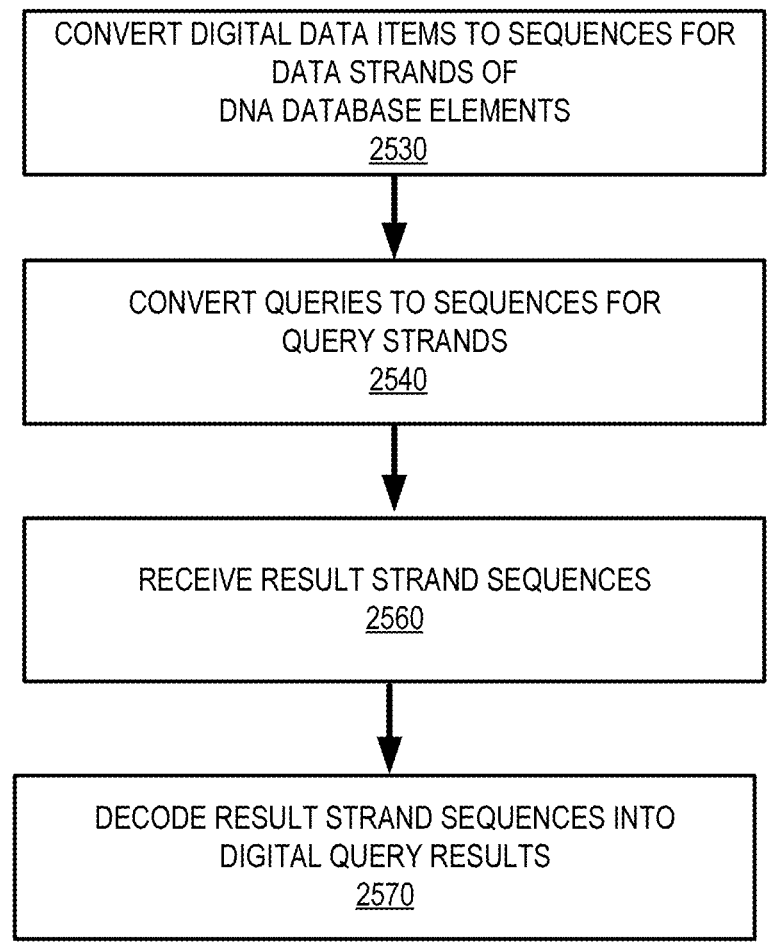
FIG. 25 is a flowchart of an example method of multiplex similarity search in DNA data storage from a digital perspective.

FIG. 25 is a flowchart of an example method 2500 of multiplex similarity search in DNA data storage from a digital perspective and can be performed, for example, by the system of FIG. 24.

At 2530, the digital data items are converted to sequences for data strands of DNA database elements. Such conversion comprises encoding a series of bits representing features (e.g., the same feature, but with different values) of the respective digital data items into digital representations of sequences which are then synthesized as a plurality of polynucleotide sequences.

At 2540, the queries are converted to sequences for DNA query strands. Such conversion comprises encoding a series of bits representing a feature query (e.g., a value to be matched) of the respective queries into digital representations of sequences which are then synthesized as a plurality of polynucleotide sequences.

At 2560, result strand sequences (e.g., digital representations of the result strands appearing in a completed query reaction run performed with the encoded polynucleotide sequences as described herein) are received.

At 2570, the result strand sequences are decoded into digital query results as described herein. The results can indicate which digital items matched which of the digital queries (e.g., they can be separated out by query).

As described herein, multiple queries (e.g., having different feature query values for a feature query) can be performed in a single reaction run.

Example 34—Example Digital Implementation of Methods

The method 2500 and any of the other digital-based methods described herein can be performed by computer-executable instructions (e.g., causing a computing system to perform the method) stored in one or more computer-readable media (e.g., storage or other tangible media) or stored in one or more computer-readable storage devices. Such methods can be performed in software, firmware, hardware, or combinations thereof. Such methods can be performed at least in part by a computing system (e.g., one or more computing devices).

The illustrated actions can be described from alternative perspectives while still implementing the technologies.

Example 35—Example Ligase Reaction

In any of the examples describing a ligation reaction herein, DNA ligase may be used to covalently bond the DNA backbone, ultimately connecting the query strand to the data strand with a linking strand. DNA ligase is a specific type of enzyme, a ligase, that facilitates the joining of DNA strands together by catalyzing the formation of a phosphodiester bond. The mechanism of DNA ligase is to form two covalent phosphodiester bonds between 3' hydroxyl ends of one nucleotide, ("acceptor") with the 5' phosphate end of another ("donor"). Ligation uses a 5' phosphate which can be added to the molecules when they are synthesized by an oligonucleotide synthesizer or added by treating the DNA with a kinase such as T4 polynucleotide kinase. A co-factor is generally involved in the reaction, and this is usually ATP or $NAD^+$. Any type of DNA ligase may be used such as *E. coli* DNA ligase, DNA ligase from bacteriophage T4, thermostable ligase from thermophilic bacteria, mammalian ligase, or the like. For optimal ligation efficiency with cohesive-ended fragments such as created by the use of staples with overhangs, the optimal enzyme temperature (e.g., 37° C. for T4 DNA ligase) is balanced with the melting temperature $T_m$ of the strands being ligated. Hybridization strands will not be stable if the temperature is high enough to disrupt hydrogen bonding between the DNA strands. A ligation reaction is most efficient when the DNA strands are already stably annealed, and disruption of the annealing ends would therefore result in low ligation efficiency. In general, the shorter the overhang, the lower the $T_m$.

Following ligation, the nicks between the strands are sealed. Sealing the nicks creates a ligation product that is a single DNA strand (which may be incorporated into a double-stranded element) which includes the original DNA strand and connected strand. This ligation product is then ready for sequencing by a sequencing technique compatible with the sequencing adaptors.

Example 36—Example Implementation: Introduction

The following "Example Implementation" sections describe an implementation with strand and codeword design schemes for a DNA database capable of approximate single-plex similarity search over a multidimensional dataset of content-rich media. Aspects of the single-plex technologies can be incorporated into the multiplex similarity search technologies described herein. The strand designs address crosstalk in associative DNA databases, and there is a method of learning DNA sequence encodings from data, which is applied to a dataset of tens of thousands of images. The design was tested in the wetlab using one hundred target images and ten query images; the tests demonstrate that the database is capable of performing similarity-based enrichment: on average, visually similar images account for 30% of the sequencing reads for each query, despite making up only 10% of the database.

DNA-based databases were first proposed over twenty years ago, yet recent demonstrations of their practicality have generated a renewed interest into researching related theory and applications.

Some recent demonstrations of DNA storage have used key-based random access for their retrieval schemes, falling short of the content-based associative searches envisioned. The described technologies can close the gap and design a DNA-based digital data store equipped with a mechanism for content-based similarity search.

The technologies contribute two advances to the field of DNA storage: first, a strand design optimized for associative search. Second, a sequence encoder capable of preserving similarity between documents, such that a query sequence generated from a given document will retrieve similar documents from the database. The designs were validated with wetlab experiments.

While the methods should generalize to databases comprising any type of media, the example focuses on images.

Example 37—Example Implementation: Overview (Similarity Search)

The problem of similarity search is to retrieve documents from a database that are similar in content to a given query. For media such as text, images and video, this can be a difficult task. Systems can convert each document into a vector-space representation using either a hand-crafted embedding, or one learned via a neural network. Such feature vectors can then be compared with metrics like Euclidean distance, where similar documents will tend to be close together in feature-space. Therefore, a similarity search can be reduced to a k-nearest-neighbor or R-near-neighbor search.

Figure 26:
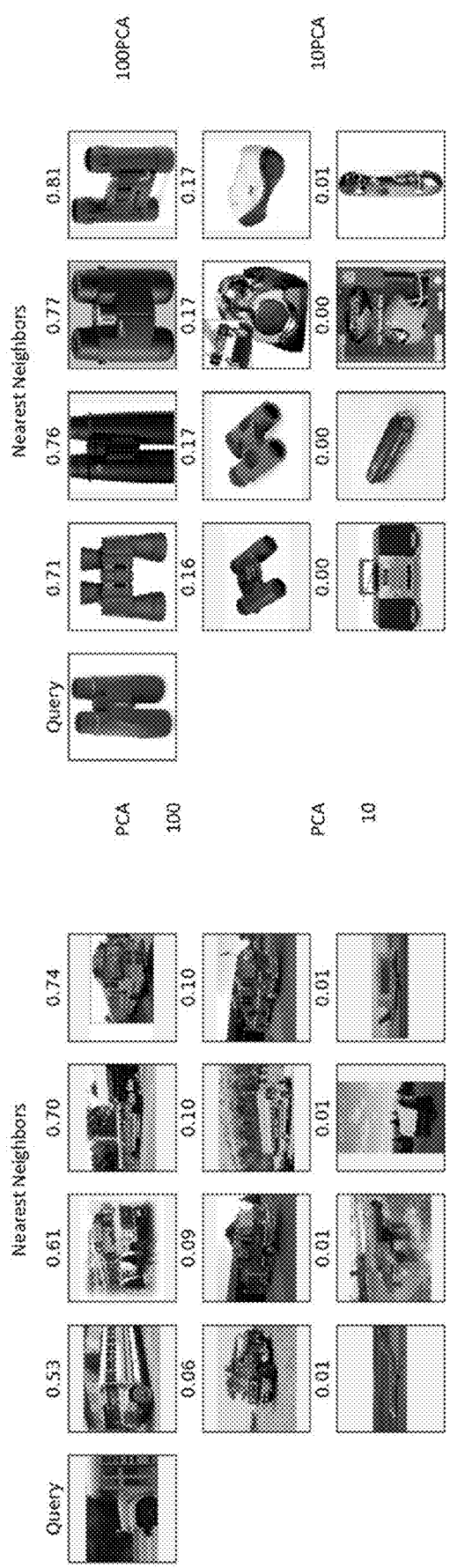
FIG. 26 is a diagram showing a pair of sample queries.

Feature vectors that are effective for similarity search tend to be high dimensional. To illustrate this, FIG. 26 shows two queries 2600 using the Caltech-256 image dataset. A pair of sample queries from the Caltech-256 dataset are depicted, showing the four nearest neighbors in three different feature spaces. Each neighbor is annotated with its Euclidean distance to the query in that space. The visual features of each image in the dataset were extracted using VGG16, a publicly available convolutional neural network trained on an image classification task. The implementation used the 4096-dimensional activations from the FC2 layer, an intermediate layer in VGG16 whose activations have shown to be effective in content-based image retrieval tasks. These features were reduced down to 100, 10, and 2 dimensions using principal component analysis (PCA). The nearest neighbors in each of these subspaces (with respect to Euclidean distance) are shown to the right of each query. Qualitatively, the nearest neighbors higher-dimensional spaces appear more similar to the query than the nearest neighbors in lower-dimensional spaces When feature vectors have hundreds of dimensions, the curse of dimensionality can defeat efficient indexing schemes. In the worst case, every item in the database must be examined to find all images within a certain distance threshold. Relaxations of the search problem that allow for errors or omissions result in much faster lookups, using algorithms such as locality-sensitive hashing (LSH).

Looking toward a future where zettabytes of data are generated every year, even techniques such as LSH that reduce the amount of data that needs to be inspected by orders of magnitude will still burden traditional storage with a tremendous number of 10 requests to a massive storage infrastructure, outstripping the time and energy cost of the feature vector distance computation itself The power required to move data from the storage device to the compute unit can be reduced by moving the compute substrate closer to the storage substrate. Such near-data processing techniques can be applied.

Example 38—Example Implementation: Overview (DNA-based Parallel Search)

DNA computing in which each DNA strand is designed to both store and process information can be thought of as an extreme version of near-data processing: the compute and storage substrates are the same.

Such a style of parallel processing requires exponential amounts of DNA to solve combinatorial problems. However, for less computationally intense problems like similarity search, the amount of DNA required is much less: if each of N items in the database is mapped to a single "target" molecule, then N identical copies of a "query" molecule are sufficient to react with every item in the database. In a single-plex implementation, if the query is equipped with a biotin tail and designed to hybridize only with relevant data, then relevant items can be "fished out" of the database using streptavidin-coated magnetic beads.

This amounts to an extremely high-bandwidth parallel search, in the vein of near-data processing techniques. Furthermore, because PCR can make exponentially many copies of the query molecule, the amount of DNA that needs to be directly synthesized is minimal. This makes DNA-based search especially appealing in the zettabyte-yottabyte future.

Example 39—Example Implementation: Overview (DNA-Based Data Storage)

DNA storage systems can focus on zero-bit-error retrieval of arbitrary digital data. Each digital file is segmented and encoded into many thousands of unique sequences, and individual files can be retrieved from a mixed database using PCR-based random access. In this implementation, one can focus on a database for storing and retrieving metadata. Instead of storing sequences that contain the complete file, each file is associated with a sequence that contains the semantic features used for content-based retrieval, as well as a pointer to the file in another database (which could be either a traditional database or a DNA-based one.

Example 40—Example Implementation: Database Design

To take advantage of the near-data processing capabilities of DNA, one can use a database design that allows each element in the database to both store and process data. One can choose to separate these two concerns by associating each database element with two sequences: one that stores an ID unique to that datum, and one that is generated from the semantic features of that datum, designed as a locus for a hybridization probe. The ID is not an "active" site, but rather the information to be retrieved by the search—for instance, it could be the address of the datum in another database that stores the document's complete data.

The simplest way to retain the association between the ID sequence and the feature sequence in a DNA database is to place them on the same strand of DNA. However, this association can cause unwanted secondary structures on longer strands, and can result in cross-talk if a query reacts with a potential target's ID sequence instead of its feature sequence.

Figure 27:
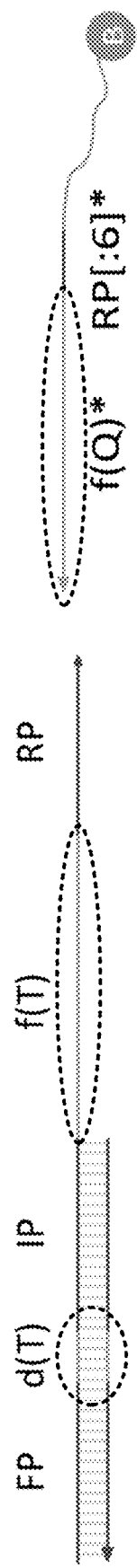
FIGS. 27A and 27B are diagrams of an example strand design.

The strand designs in the implementation address this issue, and are shown in FIGS. 27A and 27B. The encircled items indicate regions specific to the data item. Other regions are conserved. The arrow indicates the 3' end. A star (*) indicates reverse complement. RP[:6] indicates the first six bases of domain RP. The design was used in the single-plex implementation. The database entries (FIG. 27A) are synthesized single-stranded, but are made partially double stranded using a single-step PCR reaction starting from IP (the "internal primer"), which is conserved across all elements in the database. Such a technique can also be used for multiplex similarity search.

This process covers up the IP region, the ID sequence associated with the data (d(T)), and the forward primer (FP) region, which is another conserved region used to prepare samples for sequencing. This leaves the feature sequence (f(T)) and the conserved reverse sequencing primer (RP) available to interact with the query To execute a query Q, a biotinylated query strand (FIG. 27B) is mixed with the prepared targets. Because the query and target feature sequences are designed to be imperfect matches, the query strand also includes the reverse complement of the first six bases of RP (denoted RP[:6]*)—this exact match is designed to prevent misalignments and ensure that hybridization only depends on the interaction between f(T) and f(Q). The query and targets are annealed, and then streptavidin-coated magnetic beads are added to pull down targets that have hybridized with the queries.

The resulting filtered targets are amplified using FP and RP, then sequenced to retrieve the data region associated with each target.

Example 41—Example Implementation: Learned Sequence Encodings

To take advantage of the strand designs described above, one can design a mapping from images to feature domains such that a query molecule will retrieve relevant targets from the database. To simplify the task, one can pre-process all images by transforming them into the 10-dimensional subspace shown in FIG. 26, and choose the feature domains to be 30 nucleotides in length.

The general feature encoding strategy can be based on semantic hashing, where a deep neural network transforms an input feature space into an output address space where similar items are "close" together. The goal is to design a neural network sequence encoder that takes the 10-dimensional image feature vectors from the VGG16+PCA extraction process described in the "Similarity Search" Section above, and outputs DNA sequences that are close together if and only if the feature vectors are close together. One can define a pair of query and target sequences as "close" if their hybridization reaction has a high thermodynamic yield: the proportion of target molecules that are converted into a query-target duplex.

To train the neural network, one can use a loss function that will push the encoder's parameters to generate output sequences where a query retrieves a target if and only if the target and query represent similar images. One can use cross-entropy loss, where the labels are binary similarity labels (similar vs. not similar) for each pair of query and target images, and the retrieval probabilities are the thermodynamic yields of each query-target hybridization reaction. given a set of n pairs of binary labels y is an element of {0,1 and retrieval probabilities p, the cross-entropy loss is:

$$l(y, p) = -\frac{1}{n}\sum_{i=1}^{n} y_i \cdot \log(p_i) + (1 - y_i) \cdot \log(1 - p_i)$$

Using the cross-entropy loss can involve defining a binary notion of image similarity, and to define thermodynamic yield as a differentiable function of two DNA sequences. The function should be differentiable because neural networks are efficiently trained using gradient descent, which involves taking the derivative of the loss with respect to the encoder parameters.

In the sections below, a definition of binary image similarity is presented, followed by an approximation for thermodynamic yield using Hamming distance, and an approximation for Hamming distance using the cosine distance between "one-hot" encodings of DNA bases. Finally, the description presents the results of using these approximations to train a neural network on a large image dataset.

Example 42—Example Implementation: Learned Sequence Encodings

Binary Image Similarity

As described in the "Similarity Search" Section above, a semantic notion of image "similarity" can be mapped to a real-valued number by computing the Euclidean distance between two image feature vectors. However, to use the efficient cross-entropy loss function defined above, one can label image pairs with a binary label: "similar" or "not similar". One way to do this is to apply a threshold to the Euclidean distance.

Figure 28:
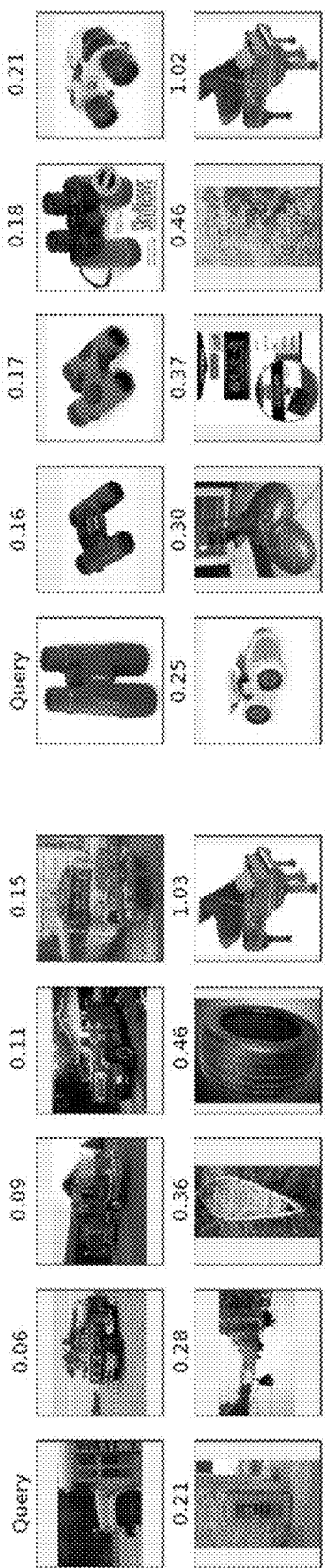
FIG. 28 is a diagram showing sample queries and image similarity.

Because the definition of similarity can be subjective, one can determine the threshold by inspection. For the feature extraction method used, it was discovered that a threshold of 0.2 to be fairly reliable across the Caltech-256 dataset. FIG. 28 demonstrates this for a pair of sample queries. FIG. 28 shows sample queries demonstrating the relationship between image similarity and distance in the 10-dimensional PCA subspace shown in FIG. 26. Distances less than 0.2 usually correspond to similar images, while those greater than 0.2 do not.

In practice, any number of other thresholds could be used.

Example 43—Example Implementation: Learned Sequence Encodings

Approximating Thermodynamic Yield

Thermodynamic yield can be calculated accurately by using the multi-stranded partition function, which is used by tools such as NUPACK. Unfortunately, this calculation is expensive and not differentiable, and thus cannot be used directly to train a neural network.

Figure 29:
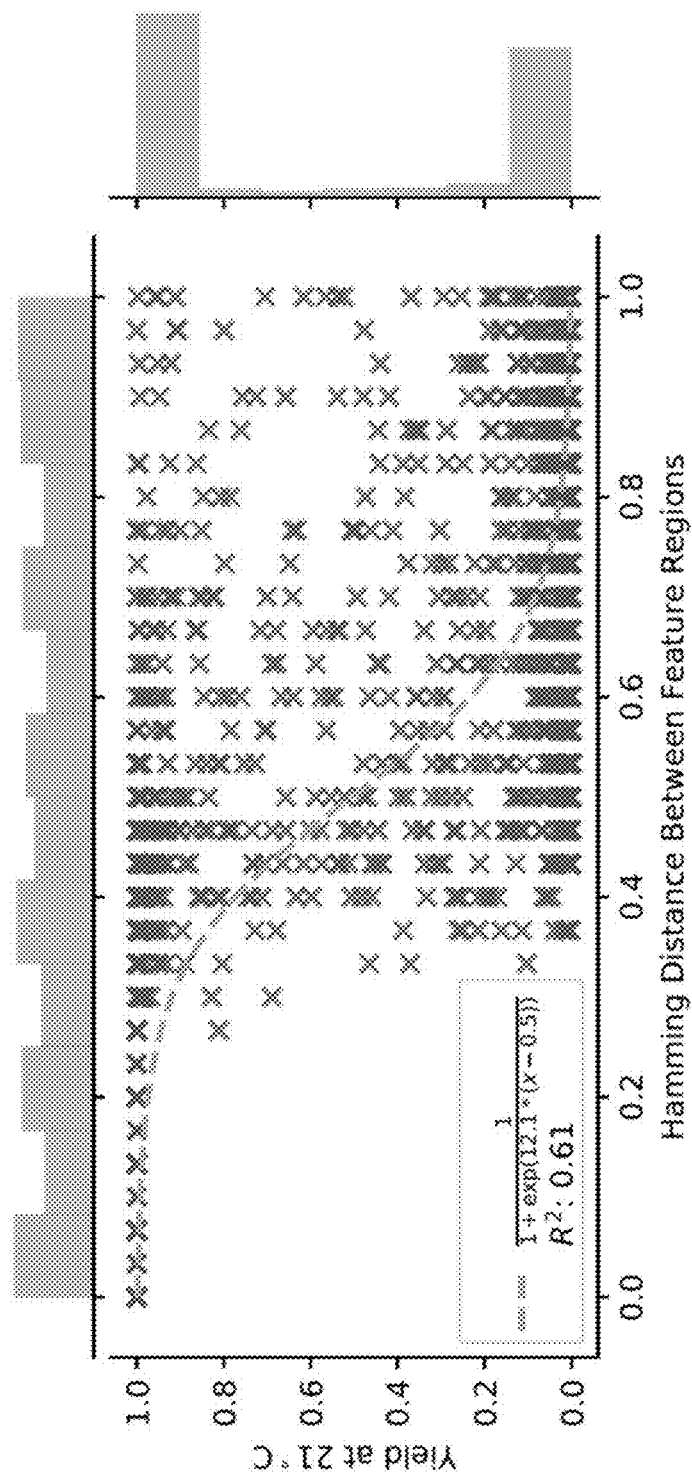
FIG. 29 is a diagram showing yield versus Hamming distance.

However, FIG. 29 shows that the query-target yield and the query-target Hamming distance have a noisy sigmoid relationship—e.g., functions of the type $$f(x) = \frac{1}{1 + \exp(ax - b)}.$$

FIG. 29 shows yield versus Hamming distance for 2000 pairs of targets and queries with feature regions of length 30, as calculated by NUPACK. The dashed line shows the best sigmoid fit to the simulations. The best fit line provides a simple approximation of thermodynamic yield in terms of the Hamming distance. A drawback is that such an approximation is less accurate for higher Hamming distances.

Example 44—Example Implementation: Learned Sequence Encodings

Approximating Hamming Distance

While one can use the Hamming distance to approximate thermodynamic yield, computing the Hamming distance requires discrete operations and is also not differentiable. Below is defined an alternative representation of DNA sequences, and a continuous approximation of Hamming distance that can be used with a neural network.

DNA sequences can be represented with a "one-hot" encoding, where each position is represented by a four-channel vector, and each channel corresponds to a base. For instance, if that base is an A, then the channel corresponding to A will have a value of one, and the other channels will be zero.

FIG. 30A shows one-hot encodings of two sequences. At each position, the one-hot encodings can be compared by computing the cosine distance between them. Given two vectors u and v, the cosine distance can be:

$$d(u, v) = 1 - \frac{u \cdot v}{\|u\| \, \|v\|}$$

If they represent different bases, the representations will be orthogonal, and the cosine distance will be one. If they represent the same base, the cosine distance will be zero. Therefore the mean cosine distance across positions will be equal to the mean number of mismatches, which is equivalent to the Hamming distance.

A neural network cannot output differentiable representations that are exactly one-hot, because this would require discretization. However, if the channel values at each position are sufficiently far apart, we can approximate a one-hot encoding by normalizing them with a softmax function, which pushes the maximum value towards one while pushing the other values towards zero. Given an N-dimensional vector u, the softmax function can be defined element-wise as follows:

$$\text{softmax}(u)_i = \frac{e^{u_i}}{\sum_{j=1}^{N} e^{u_j}}$$

Furthermore, one can encourage the channel values to be far apart by using a hidden-layer activation function with a large output range, such as the rectified linear unit (ReLU) function. The ReLU function can be defined as:

$$\text{ReLU}(x) = \max(x, 0)$$

FIG. 30B shows the relationship between the mean cosine distance and Hamming distance of pairs of outputs, for 10,000 pairs of random inputs to a randomly initialized neural network with 10 input units, two ReLU hidden layers of 128 units each, and 30 four-channel softmax output units. The mean cosine distance between the neural network outputs closely follows the Hamming distance between their discretized counterparts, validating our approximation. Such a four-channel encoding technique can be used.

Example 45—Example Implementation: Learned Sequence Encodings

Neural Network Architecture

Figure 31:
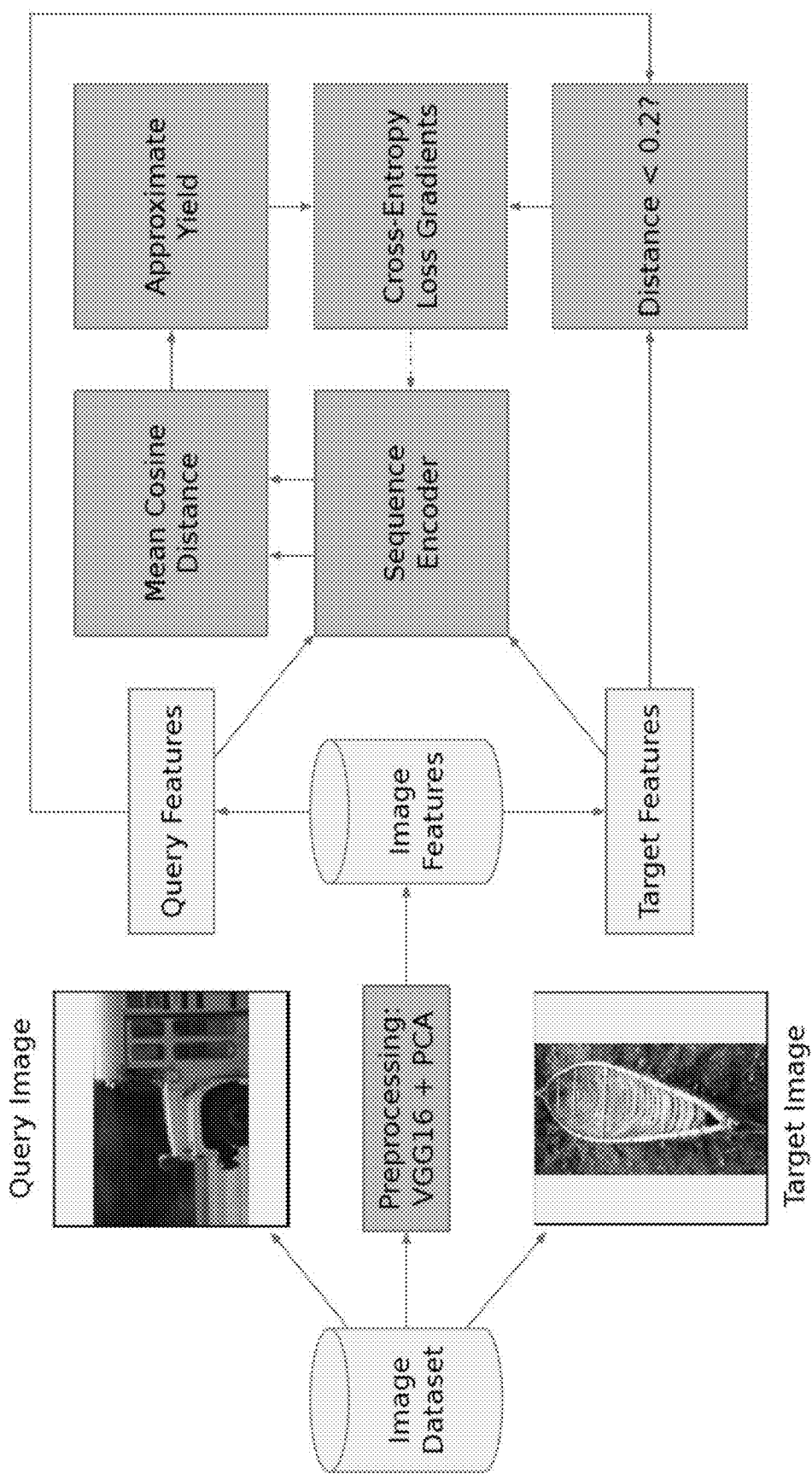
FIG. 31 is a diagram of a training loop.

Composing the yield approximation with the Hamming distance approximation allows one to use gradient descent to train any kind of neural-network-based sequence encoder to generate good encodings for similarity search, given a suitable dataset. This process is depicted in FIG. 31. FIG. 31 shows a training loop, illustrating how a pair of images is used to calculate gradients for the sequence encoder. Data is in light gray, and operations are in dark gray. On each iteration, a pair of images is encoded, and then the mean cosine distance between the outputs is used to calculate the approximate thermodynamic yield. Combined with the actual similarity between the feature vectors, the parameters of the neural network are updated using the gradient of the cross-entropy loss with respect to the parameters.

The design space of neural-network-based sequence encoders could be explored for alternatives. In the implementation, a small-scale exploration was conducted and the architecture depicted in FIG. 32 was used, but any number of alternatives could be used.

The network begins with two convolutional layers, where each input dimension is processed independently with a shared set of weights. This was done to preserve some of the "element-wise" structure of the Euclidean distance used to calculate the similarity label. The first convolutional layer has a sine-function activation, based on spectral hashing, a method for transforming an input feature space into a binary address space. The second convolutional layer uses the ReLU function to allow the outputs to be further apart.

Since the input dimensions do not have a spatial interpretation, one can cap the convolutional layers with a set of fully connected weights to the four-channel sequence output, such that each input dimension's activation map is given a chance to influence each base in all positions. A ReLU activation followed by a softmax activation gives us the approximate one-hot representation discussed above.

Example 46—Example Implementation: Learned Sequence Encodings

Training Results

To train the encoder, the implementation first split the 30,607 images of the Caltech256 dataset into 24,485 training images and 6,122 test images. The implementation extracted the VGG16 FC2 features from all 30,607 images, and then fitted a PCA transform to the FC2 vectors from the training set. The fitted transform was applied to all images.

Figure 33:
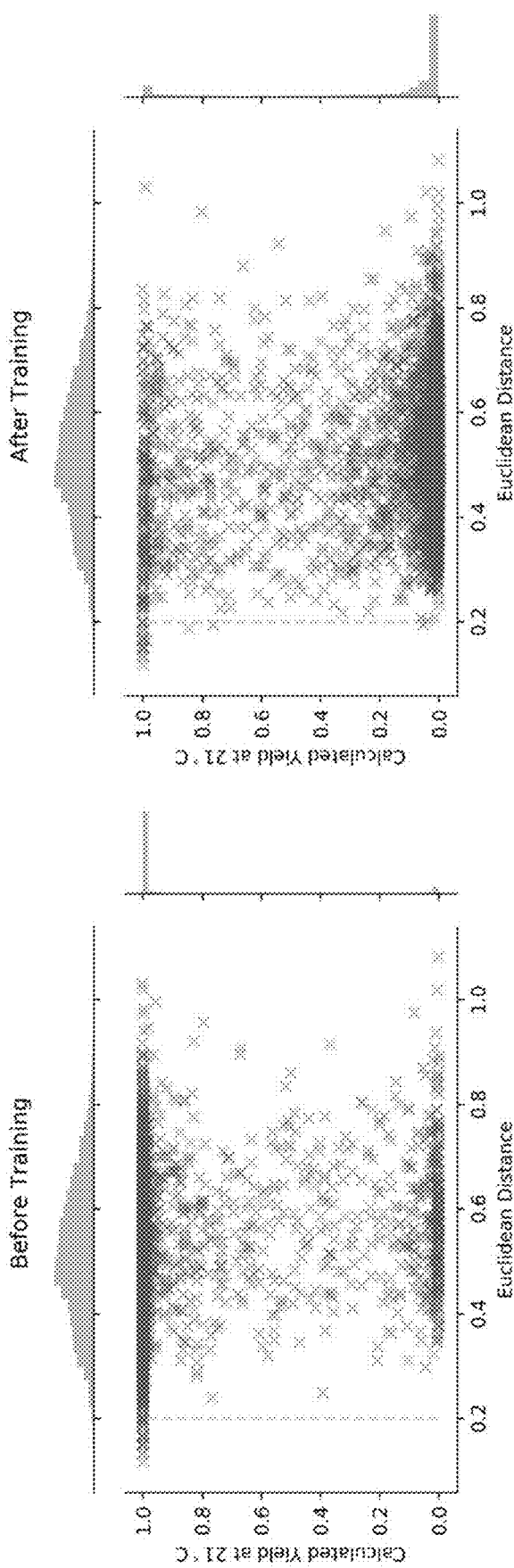
FIG. 33 is a diagram showing encoder performance.

During each training iteration, a batch of random pairs of training set images was used to update the encoder weights, as depicted in FIG. 31. The encoder was trained for 65,000 iterations using 500 random pairs of images per iteration. FIG. 33 shows the performance of the encoder as measured by the relationship between the thermodynamic yield (calculated with NUPACK) and the Euclidean distance between the images in the pair. NUPACK was set to simulate the experimental setup, with an equal molar ratio of target to query strands, and temperature at 21° C. FIG. 33 shows encoder performance on 3000 pairs of images from the test set, before and after training. The x-axis is the Euclidean distance between the target and the query, and the y-axis is the thermodynamic yield (calculated with NUPACK). The dotted line shows the similarity threshold of 0.2

The performance is shown before training (with random parameters), and again after training. Before training, nearly all pairs of images exhibit a high yield, indicating no selectivity by distance. After training, most pairs have a low yield, but almost no pairs of images under 0.2 in Euclidean distance (which has been defined as similar) have a low yield. However, there are still non-similar images that have high yield, indicating that any successful query will also retrieve non-similar images.

Example 47—Example Implementation: Experiments

Dataset Construction

To test the designs in the wetlab, a subset of the test set was constructed consisting of 10 query images and 100 target images. The queries were chosen by first clustering all images in the training set into 10 groups using k-means, and then choosing a representative query image from the test set that belonged to each cluster. The k-means step ensures that none of the query images are pairwise-similar, because they all belong to different clusters in the data.

Figure 34:
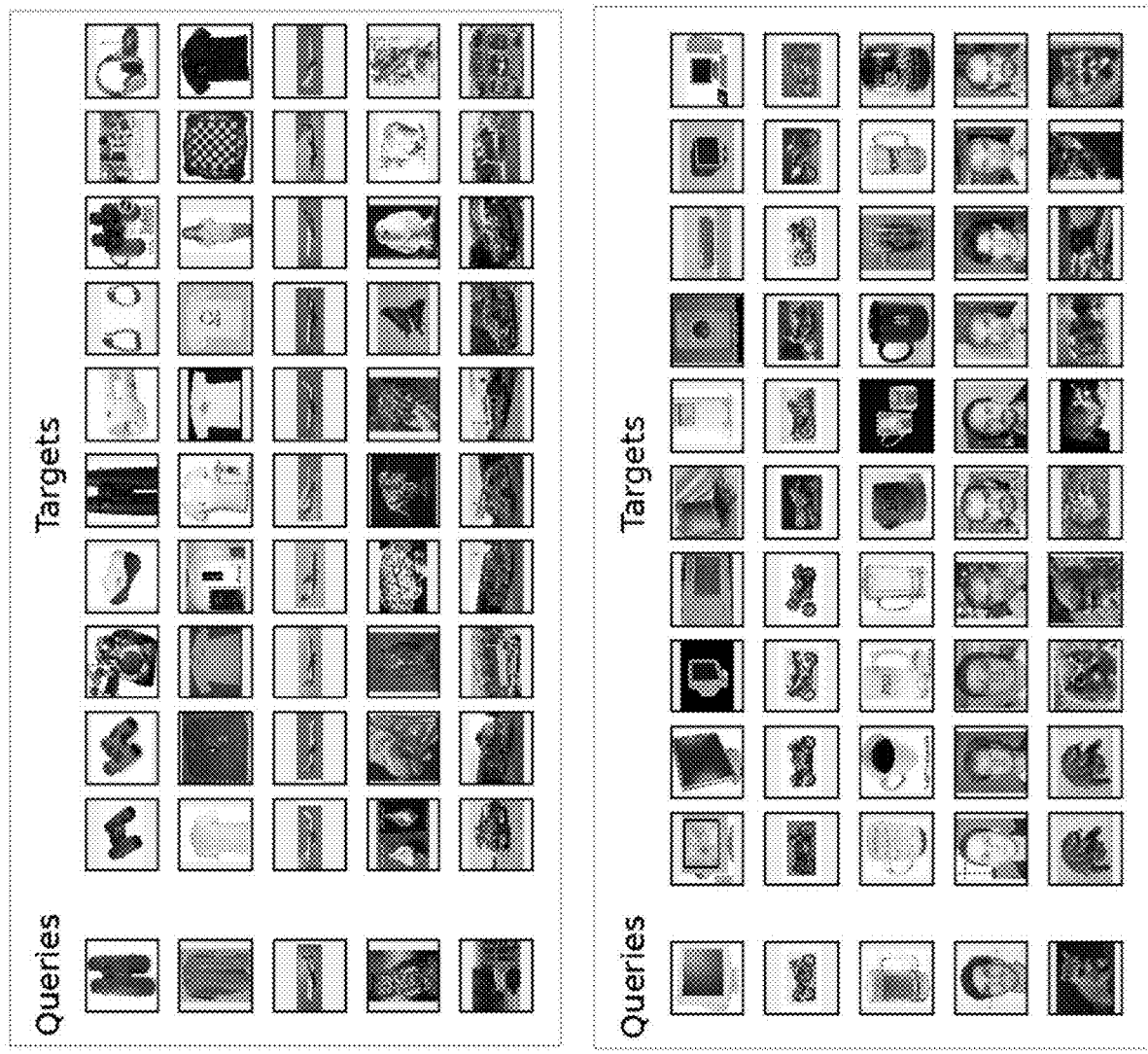
FIG. 34 is a diagram showing a set of query and target images used in wetlab experiments.

For each of these 10 query images, its 10 nearest neighbors were selected in the test set. This ensures that each query image has 10 similar images and 90 dissimilar images among the 100 targets. The result of this selection process is shown in FIG. 34.

For each image, its features were encoded as a 30-nucleotide DNA sequence using the trained encoder, as described in the "Training Results" Section. For each target image, it was assigned a random 5-nt ID, and then a 90-nt sequence was constructed as shown in FIG. 27A. For each query image, a 36-nt sequence was constructed as shown in FIG. 27B. Target and query strands were then ordered from IDT. The query strands included the addition of a biotinylated spacer at the 5' end.

Example 48—Example Implementation: Experiments

Target Preparation

All target strands were mixed together in an equal molar ratio. The targets were then mixed with 20% excess of the primer IP* at 10 µM, and 20 µL of the target-primer mixture was added to 20 µL of 2×KAPA HIFI PCR enzyme mix. This 40 µL mixture was placed in a thermocycler with the following protocol: (1) 95° C. for 3 minutes, (2) 98° C. for 20 seconds, (3) 56° C. for 20 seconds, (4) 72° C. for 20 seconds, (5) go to step 2 one more time, and (6) 72° C. for 30 seconds. This process extends the primer to cover the 5' half of each target strand.

Example 49—Example Implementation: Experiments

Query Protocol

For each of the 10 query strands, a sample of the target mixture was diluted to 200 nM and mixed with an equal molar concentration of the query, then annealed in a thermocycler from 95° C. to 21° C. at a rate of 1° C. per minute.

The annealed query-target mixture was mixed with streptavidin-coated magnetic beads, incubated at room temperature for 15 minutes, and placed on a magnetic rack. The supernatant containing non-captured DNA was removed and the beads were resuspended in elution buffer (resuspended after several times of bead wash), then incubated for 5 min at 95° C. and placed on a magnetic rack to separate captured DNA molecules from biotinylated query strands. The supernatant containing the captured DNA was mixed with the forward primer FP and the reverse primer RP* in a PCR reaction to amplify the captured targets. The amplified targets were ligated with Illumina sequencing adapters and then sequenced using an Illumina NextSeq.

This procedure was repeated 3 times for each of the 10 queries. Each query and replicate was given a unique sequencing index.

Example 50—Example Implementation: Experiments

Results

For each query and replicate, the reads were aligned with the set of all target sequences using BWA-MEM. Li, H., "Aligning sequence reads, clone sequences and assembly contigs with BWA-MEM" (2013). FIG. 35A shows the number of aligned reads for each target versus the distance from that target to the query, for two sample queries, and for all queries together. FIG. 35A shows the number of aligned reads per target vs. distance from target to query. Points indicate the mean across three replicates, and error bars indicate standard error. Different shades indicate different query images.

FIG. 35B shows the cumulative distribution of aligned reads as a function of distance from the query. FIG. 35B shows cumulative distribution of aligned reads as a function of increasing distance from target to query. For reference, the dashed lines show the cumulative distribution of targets by distance, and the dotted lines show an ideal where all reads are allocated to the nearest targets. Different shades indicate different query images (grey in the last graph for all queries). The dashed line is a baseline indicating the cumulative distribution of distances across the targets. The further the solid line is from the baseline, the stronger the relationship between distance and the number of reads. The dotted line shows the ideal result, where reads are only allocated to similar targets (those less than 0.2 Euclidean distance from the query).

The first sample query (the binoculars) shows a successful result, where most of the reads are allocated to similar targets. In contrast, the second sample query (the school bus) is less successful: the reads are distributed almost evenly across similar and non-similar images.

Across all queries, the results were moderately successful—though there are many reads going to dissimilar targets, the scheme is clearly capable of performing similarity-based enrichment: roughly 30% of the sequencing resources are being used by similar targets, which by construction make up just 10% of the database.

Example 51—Example Implementation: Further Description

In practice, the 10-dimensional image feature subspace used for the experiments is insufficiently selective. Referring back to FIG. 26, the 100-dimensional space was more effective at relating distance to qualitative similarity. But it is difficult to train an encoder to transform this already-compressed 100-dimensional subspace into a 30-nucleotide feature sequence.

Figure 36:
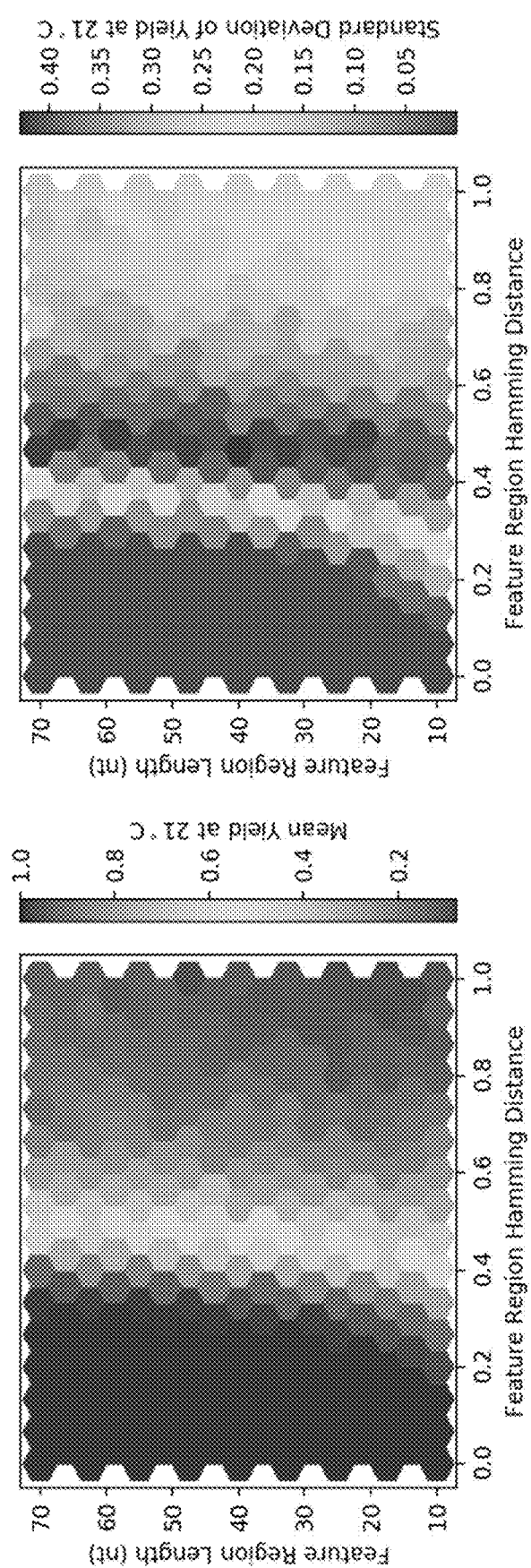
FIG. 36 is a diagram showing mean and standard deviation of yield as a function of feature region length and feature region Hamming distance.

One might be tempted to try longer feature regions, but this will likely experience more noise of the type seen in the results. FIG. 36 illustrates this by generalizing FIG. 29 to feature regions of different sizes. These plots bin across sequence length and target-query Hamming distance, and the color shade indicates either the mean (on the left) or the standard deviation (on the right) of the yield values in that bin, at our protocol temperature of 21° C. These plots tell us that selectivity decreases with increasing length, and that variance in yield for dissimilar targets increases as well.

These problems pose a difficult challenge to scaling this system. One improvement is to use a more accurate approximation for thermodynamic yield that can still be used to train a neural network. Another is to explore alternative probe designs that are meant to reduce variance, such as toehold exchange probes. Wu, L. R., Wang, J. S., Fang, J. Z., R Evans, E., Pinto, A., Pekker, I., Boykin, R., Ngouenet, C., Webster, P. J., Beechem, J., Zhang, D. Y., "Continuously tunable nucleic acid hybridization probes," *Nature Methods* 12(12), 1191-1196 (2015), Zhang, D. Y., Chen, S. X., Yin, P., "Optimizing the specificity of nucleic acid hybridization," *Nature Chemistry* 4(3), 208-214 (2012).

Example 52—Example Computing Systems

Figure 37:
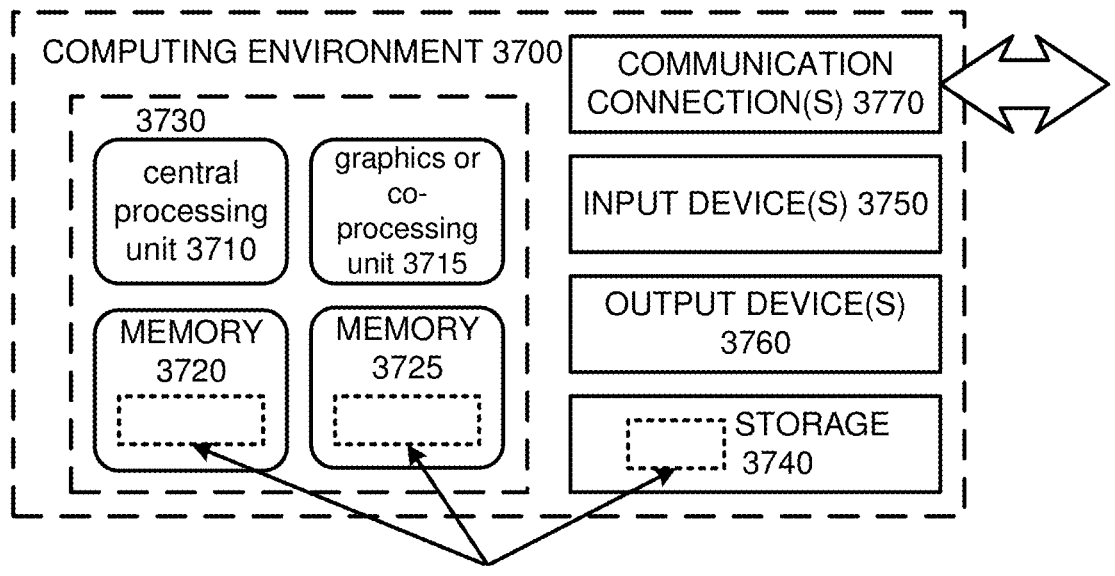
FIG. 37 is a block diagram of an example computing system in which described embodiments can be implemented.

FIG. 37 depicts an example of a suitable computing system 3700 in which digital aspects of the described innovations can be implemented. The computing system 3700 is not intended to suggest any limitation as to scope of use or functionality of the present disclosure, as the innovations can be implemented in diverse computing systems.

With reference to FIG. 37, the computing system 3700 includes one or more processing units 3710, 3715 and memory 3720, 3725. In FIG. 37, this basic configuration 3730 is included within a dashed line. The processing units 3710, 3715 execute computer-executable instructions, such as for implementing the features described in the examples herein. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 37 shows a central processing unit 3710 as well as a graphics processing unit or co-processing unit 3715. The tangible memory 3720, 3725 can be volatile memory (e.g., registers, cache, RAM), non-volatile memory (e.g., ROM, EEPROM, flash memory, etc.), or some combination of the two, accessible by the processing unit(s) 3710, 3715. The memory 3720, 3725 stores software 3780 implementing one or more innovations described herein, in the form of computer-executable instructions suitable for execution by the processing unit(s) 3710, 3715.

Functionality can also be performed, at least in part, by one or more hardware logic components. For example, Field-programmable Gate Arrays (FPGAs), Application-specific Standard Products (ASSPs), System-on-a chip systems (SOCs), Complex Programmable Logic Devices (CPLDs), and the like can be used.

A computing system 3700 can have additional features. For example, the computing system 3700 includes storage 3740, one or more input devices 3750, one or more output devices 3760, and one or more communication connections 3770, including input devices, output devices, and communication connections for interacting with a user. An interconnection mechanism (not shown) such as a bus, controller, or network interconnects the components of the computing system 3700. Typically, operating system software (not shown) provides an operating environment for other software executing in the computing system 3700, and coordinates activities of the components of the computing system 3700.

The tangible storage 3740 can be removable or non-removable, and includes magnetic disks, magnetic tapes or cassettes, CD-ROMs, DVDs, or any other medium which can be used to store information in a non-transitory way and which can be accessed within the computing system 3700. The storage 3740 stores instructions for the software 3780 implementing one or more innovations described herein.

The input device(s) 3750 can be an input device such as a keyboard, mouse, pen, or trackball, a voice input device, a scanning device, touch device (e.g., touchpad, display, or the like) or another device that provides input to the computing system 3700. The output device(s) 3760 can be a display, printer, speaker, CD-writer, or another device that provides output from the computing system 3700.

The communication connection(s) 3770 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer and should not be confused with acts performed by a human being. The actual computer operations corresponding to these terms vary depending on implementation.

Example 53—Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing system to perform the method. The technologies described herein can be implemented in a variety of programming languages.

Example 54—Example Cloud Computing Environment

Figure 38:
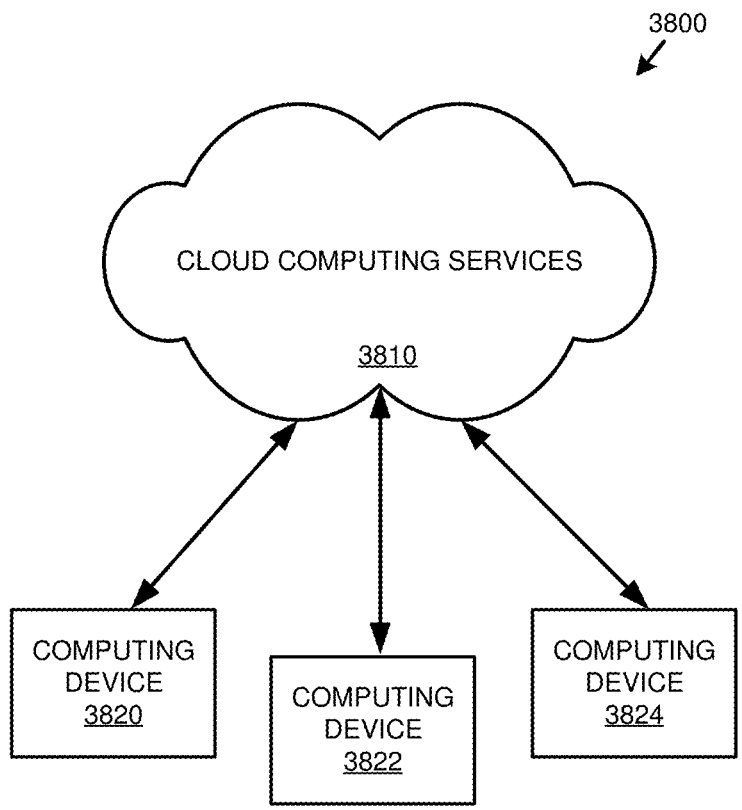
FIG. 38 is a block diagram of an example cloud computing environment that can be used in conjunction with the technologies described herein.

FIG. 38 depicts an example cloud computing environment 3800 in which the described technologies can be implemented, including, e.g., the system 100 of FIG. 1 and other systems herein. The cloud computing environment 3800 comprises cloud computing services 3810. The cloud computing services 3810 can comprise various types of cloud computing resources, such as computer servers, data storage repositories, networking resources, etc. The cloud computing services 3810 can be centrally located (e.g., provided by a data center of a business or organization) or distributed (e.g., provided by various computing resources located at different locations, such as different data centers and/or located in different cities or countries).

The cloud computing services 3810 are utilized by various types of computing devices (e.g., client computing devices), such as computing devices 3820, 3822, and 3824. For example, the computing devices (e.g., 3820, 3822, and 3824) can be computers (e.g., desktop or laptop computers), mobile devices (e.g., tablet computers or smart phones), or other types of computing devices. For example, the computing devices (e.g., 3820, 3822, and 3824) can utilize the cloud computing services 3810 to perform computing operations (e.g., data processing, data storage, and the like).

In practice, cloud-based, on-premises-based, or hybrid scenarios can be supported.

Example 55—Example Implementations

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.

Example 56—Example Embodiments

Any of the following embodiments can be implemented.

Clause A. A method comprising:

in a single multiplex similarity search query reaction run comprising a plurality of DNA database elements implementing DNA data storage, matching a query strand to a DNA database element, wherein the matching comprises hybridizing a feature nucleotide sequence of the DNA database element to a complementary feature nucleotide sequence of the query strand, and the matching comprises arranging a DNA linking strand into a connection between a data strand of the DNA database element and the query strand, wherein the arranging produces a DNA result element comprising a result strand comprising the query strand and the data strand;

sequencing the result strand comprising the query strand and the data strand, wherein the sequencing yields a digital representation of an identifier region of the query strand and a digital representation of an identifier region of the data strand of the matched DNA database element, thereby indicating a digital query and a digital data item matching the digital query;

wherein the single multiplex similarity search query reaction run comprises matching query strands having different complementary feature nucleotide sequences to different DNA database elements.

Clause B. The method of clause A, wherein the sequencing generates results for a plurality of result strands representing a plurality of digital queries, and the method further comprises:

separating results of the plurality of result strands by digital query.

Clause C. The method of any of clauses A-B further comprising:

mapping digital representations of feature regions of query strands to respective digital queries for which the query strands were created.

Clause D. The method of any of clauses A-C wherein:

the query strands having different complementary feature nucleotide sequences represent respective, different digital queries.

Clause E. The method of clause any of clauses A-D further comprising:

for the respective, different digital queries, identifying which of a plurality of digital data items represented in the single similarity search query reaction run match the respective, different digital queries.

Clause F. The method of clause E wherein the identifying comprises:

for a given result strand, identifying an address of a digital data item encoded on the given result strand and identifying a query identifier encoded on the given result strand.

Clause G. The method of clause any of clauses A-F further comprising:

after sequencing the result strand comprising the query strand and the data strand, mapping the digital representation of the identifier region of the query strand to a digital query for which the query strand was created.

Clause H. The method of clause G further comprising:

for at least one other result strand, mapping a digital representation of an identifier region of a query strand to a different digital query for which the query strand was created.

Clause I. The method of clause any of clauses A-H wherein:
  a plurality of the different DNA database elements represent respective, different underlying digital data items.
Clause J. The method of clause any of clauses A-I further comprising:
  completing the connection between the data strand of the DNA database element and the query strand, wherein completing the connection comprises performing a ligation reaction.
Clause K. The method of clause any of clauses A-J further comprising:
  identifying an underlying digital data item matching the digital query, wherein identifying the underlying digital data item comprises mapping the identifier region of the data strand to the underlying digital data item.
Clause L. The method of clause K further comprising:
  selecting the underlying digital data item for further processing.
Clause M. The method of clause K further comprising:
  displaying the underlying digital data item.
Clause N. The method of clause any of clauses A-M further comprising:
  amplifying the result strand.
Clause O. The method of clause any of clauses A-N further comprising:
  synthesizing the data strand, wherein the data strand comprises an internal primer; and
  generating the DNA database element, wherein the generating comprises:
  covering the identifier region of the data strand via the internal primer.
Clause P. The method of clause any of clauses A-O wherein:
  the feature nucleotide sequence of the DNA database element and the complementary feature nucleotide sequence of the query strand are generated by a trained neural network.
Clause Q. The method of clause P wherein:
  the trained neural network is trained based on a four-channel vector representation of DNA sequence positions.
Clause R. A DNA database comprising:
  a collection of DNA database elements representing respective digital database items; and
  a collection of query strands representing respective queries targeting the digital database items via different reverse complementary query sequences;
  wherein at least one of the DNA database elements and at least one of the query strands are connected via a DNA linking strand, whereby multiplex similarity search in DNA data storage is performed.
Clause S. One or more non-transitory computer-readable media comprising:
  computer-executable instructions capable of converting digital data items sequences for data strands of DNA database elements;
  computer-executable instructions capable of converting a plurality of digital queries to a plurality of respective sequences for query strands;
  computer-executable instructions capable of receiving result strand sequences generated by a completed query reaction run performed with the DNA database elements and the query strands; and
  computer-executable instructions capable of decoding the result strand sequences into digital query results, wherein the digital query results indicate which digital data items matched which of the plurality of digital queries.
Clause T. The one or more non-transitory computer-readable media of clause S wherein converting digital queries to sequences for query strands comprises:
  for a given digital query specifying a value of a feature, calculating a complementary query feature sequence; and
  calculating a query strand sequence comprising the complementary query feature sequence.

Example 57—Example Alternatives

The technologies from any example can be combined with the technologies described in any one or more of the other examples. In view of the many possible embodiments to which the principles of the disclosed technology can be applied, it should be recognized that the illustrated embodiments are examples of the disclosed technology and should not be taken as a limitation on the scope of the disclosed technology. Rather, the scope of the disclosed technology includes what is covered by the scope and spirit of the following claims.

What is claimed is:
1. A method comprising:
  in a single multiplex similarity search query reaction run comprising a plurality of DNA database elements implementing DNA data storage, matching a query strand to a DNA database element, wherein the matching comprises hybridizing a feature nucleotide sequence of the DNA database element to a complementary feature nucleotide sequence of the query strand serving as an identifier region, the query strand is one out of a plurality of query strands representing different queries in the single multiplex similarity search query reaction run, and the matching comprises arranging a DNA linking strand into a connection between a data strand of the DNA database element and the query strand, wherein the arranging produces a DNA result element comprising a result strand comprising the query strand and the data strand;
  sequencing the result strand comprising the query strand and the data strand, wherein the sequencing yields a digital representation of the identifier region of the query strand and a digital representation of an identifier region of the data strand of the matched DNA database element, thereby indicating a digital query and a digital data item matching the digital query;
wherein:
the single multiplex similarity search query reaction run comprises matching query strands having different complementary feature nucleotide sequences to different DNA database elements;
an identifier sequence d(T) of the data strand uniquely identifies the data strand, maps the data strand to its underlying digital item, and differentiates the data strand from other data strands representing other digital data items;
a complementary feature sequence f(Q)* serves as an identifier of the query strand and thus an identifier of an underlying digital query, facilitating multiplex query operation by allowing determination of the underlying digital query that generated a particular result strand among result strands generated by one or more other digital feature queries, thereby differentiating the underlying digital query of the result strand from the other digital feature queries; and the result strand comprises both the identifier sequence d(T) of the data strand uniquely identifying the data strand and the complementary feature sequence f(Q)* of the query strand identifying the underlying digital query and differentiating the underlying digital query of the result strand from the other digital feature queries.

2. The method of claim 1, wherein the sequencing generates results for a plurality of result strands representing a plurality of digital queries, and the method further comprises:

separating results of the plurality of result strands by digital query.

3. The method of claim 1 further comprising:

mapping digital representations of feature regions of query strands to respective digital queries for which the query strands were created.

4. The method of claim 1 wherein:

the query strands having different complementary feature nucleotide sequences represent respective, different digital queries.

5. The method of claim 4 further comprising:

for the respective, different digital queries, identifying which of a plurality of digital data items represented in the single similarity search query reaction run match the respective, different digital queries.

6. The method of claim 5 wherein the identifying comprises:

for a given result strand, identifying an address of a digital data item encoded on the given result strand and identifying a query identifier encoded on the given result strand.

7. The method of claim 1 further comprising:

after sequencing the result strand comprising the query strand and the data strand, mapping the digital representation of the identifier region of the query strand to a digital query for which the query strand was created.

8. The method of claim 7 further comprising:

for at least one other result strand, mapping a digital representation of an identifier region of a query strand to a different digital query for which the query strand was created.

9. The method of claim 1 wherein:

a plurality of the different DNA database elements represent respective, different underlying digital data items.

10. The method of claim 1 further comprising:

completing the connection between the data strand of the DNA database element and the query strand, wherein completing the connection comprises performing a ligation reaction.

11. The method of claim 1 further comprising:

identifying an underlying digital data item matching the digital query, wherein identifying the underlying digital data item comprises mapping the identifier region of the data strand to the underlying digital data item.

12. The method of claim 11 further comprising:

selecting the underlying digital data item for further processing.

13. The method of claim 1 further comprising:

amplifying the result strand.

14. The method of claim 1 further comprising:

synthesizing the data strand, wherein the data strand comprises an internal primer; and generating the DNA database element, wherein the generating comprises:

covering the identifier region of the data strand via the internal primer.

15. The method of claim 1 wherein:

the feature nucleotide sequence of the DNA database element and the complementary feature nucleotide sequence of the query strand are generated by a trained neural network.

16. The method of claim 15 wherein:

the trained neural network is trained based on a four-channel vector representation of DNA sequence positions.

17. The method of claim 1 wherein:

the result strand is of longer length than other strands in the reaction run; and the method further comprises:

filtering the result strand based on length.

18. The method of claim 1 wherein:

the digital query comprises a same digital query having a plurality of similarity search results, the similarity search results having respective different identities; and a decoder determines the different identities of different digital data items matching the same digital query.

19. The method of claim 1, wherein the method further comprises:

binding the DNA linking strand to the query strand, wherein the binding yields a query-linking element; and binding the query-linking element to the DNA database element.

20. The method of claim 1, wherein the method further comprises:

binding the query strand to the DNA database element, wherein the binding yields a preliminary result strand; and binding the DNA linking strand to the preliminary result strand.

* * * * *